(12) United States Patent
Solomon et al.

(10) Patent No.: US 7,094,945 B2
(45) Date of Patent: Aug. 22, 2006

(54) OSR-1 NUCLEIC ACIDS AND PROTEINS

(75) Inventors: Aaron Solomon, Evanston, IL (US);
Richard Morimoto, Evanston, IL (US);
Greg Beitel, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/736,868

(22) Filed: Dec. 16, 2003

(65) Prior Publication Data

US 2005/0079160 A1    Apr. 14, 2005

Related U.S. Application Data

(60) Provisional application No. 60/443,819, filed on Dec. 16, 2002.

(51) Int. Cl.
*A01K 67/033* (2006.01)
*C07H 21/02* (2006.01)
*C12N 15/85* (2006.01)

(52) U.S. Cl. .................. 800/8; 536/24.5; 435/320.1
(58) Field of Classification Search .................. None
See application file for complete search history.

(56) References Cited

OTHER PUBLICATIONS

Piggott et al., "Hypo-osmotic regulation in entomopathogenic nematodes: *Steinernema* spp. and *heterorhabditis* spp.," Nematol. 2(5): 561-566, 2000.*
Ogg et al., "The Fork head transcription factor DAF-16 transduces insulin-like metabolic and longevity signals in *C. elegans*," Nature 389: 994-999, Oct. 1997.*
O'Leary et al., "The Isolation of mutants of *Heterorhabditis megidis* (strain UK211) with increased desiccation tolerance," Fundam. Appl. Nematol. 20(2): 197-205, 1997.*
Solomon, et al. "Desiccation Tolerance Of *Muellerius CF. Capillaris* (Nematoda: Protostronylidae) First Stage Larvae" J Parasitology 84: 802-805 (1998).
Solomon, et al. "Migratory Behaviour and Desiccation Tolerance of Protostrongylid Nematode First-Stage Larvae" Int J Parasitology 27: 1517-1522 (1997).
Solomon, et al."Desiccation Survival of the Entomopathogenic Nematode *Steinernema feltiae*: Induction of Anhydrobiosis", Nematology 1: 61-68 (1999).
Kaya and Gaugler, "Entomopathogenic Nematodes" Annual Review of Entomology 38: 181-206, (1993).
Colbert et al., "OSM-9, A Novel Protein with Structural Similarity to Channels, Is Required for Olfaction, Mechanosensation, and Olfactory . . . " J Neursci. 17: 8259-8269 (1997).
Culotti et al., "Osmotic Avoidance Defective Mutants of the Nematode *Caenorhabditis elegans*" Genetics 90: 243-256 (1978).
Hart et al., "Distinct Signaling Pathways Mediate Touch and Osmosensory Responses in a Polymodal Sensory Neuron" J Neurosci 19: 1952-1958 (1999).
Lithgow et al., "Thermotolerance and Extended Life-Span Conferred by single-gene mutations and induced by thermal stress" Proc Natl Acad Sci U.S.A. 92: 7540-7544 (1995).

Lee et al., "A systematic RNAi screen identifies a critical role for mitochondria in *C. elegans* longevity" Nat Genetics 33:40-48 (2003).
Henderson and Johnson, "daf-16 integrates developmental and environmental inputs to mediate aging in the nematode *Caenorhabditis elegans*" Curr Biol 11: 1975-1980 (2001).
Murakami and Johnson, "A Genetic Pathway Conferring Life Extension and Resistance to UV Stress in *Caenorhabditis elegans*" Genetics 143: 1207-1218 (1996).
Tobin et al., "Combinatorial Expression of TRPV Channel Proteins Defines Their Sensory Functions and Subcellular Localization in *C. elegans* Neurons" Neuron 35: 307-318 (2002).
Kaplan and Horvitz, "A dual mechanosensory and chemosensory neuron in *Caenorhabditis elegans*" Proc Natl Acad Sci U.S.A. 90: 2227-2231 (1993).
Wang et al., "The expression of TGFB signal transducers in the hypodermis regulates body size in *C. elegans*" Development 129: 4989-4998 (2002).
Petalcorin et al., "Disruption of clh-1, a Chloride Channel Gene, Results in a Wider Body of *Caenorhabditis elegans*" J Mol Biol 294: 347-355 (1999).
Kurz and Ewbank, "*Caenorhabditis elegans*: An emerging genetic model for the study of innate immunity" Nat Rev Genet 4: 380-390 (2003).
Sagasti et al., "The CaMKII UNC-43 Activates the MAPKKK NSY-1 to Execute a Lateral Signaling Decision Required for Asymetric Olfactory Neuron Fates" Cell 105: 221-232 (2001).
Tanaka-Hino et al., "SEK-1 MAPKK mediates Ca2+ signaling to determine neuronal asymmetric development in *Caenorhabditis elegans*" EMBO Rep 3: 56-62 (2002).
Reiner et al., "Diverse behavioural defects caused by mutations in Caenorhabditis elegans unc-43 CaM Kinase II" Nature 402: 199-203 (1999).
Villanueva et al., "jkk-1 and mek-1 regulate body movement coordination and response to heavy metals through jnk-1 in *Caenorhabditis elegans*" EMBO 20(18):5114-5128 (2001).
Koga et al., "A *Caenorhabditis elegans* MAP kinase kinase, MEK-1, is involved in stress responses" Embo J 19: 5148-5156 (2000).
Solomon et al. "Desiccation tolerance of *Muellerius capillaris* first-stage larvae from Israeli arid and French temperate habitats and their . . . " Parasitology 119: 621-626 (1999).

* cited by examiner

*Primary Examiner*—Scott D. Priebe
(74) *Attorney, Agent, or Firm*—Medlen & Carroll, LLP

(57) ABSTRACT

The present invention relates to water-stress tolerance, in particular to the OSR-1 (osmotic stress resistant-1) protein, and nucleic acids encoding the OSR-1 protein. The present invention provides assays for the detection of OSR-1, and polymorphisms and mutations associated with water stress tolerance. In particular, the present invention relates to compositions comprising small interfering RNA duplexes (RNAi), or vectors that encode dsRNA, that inhibit expression of the OSR-1 gene (e.g. by targeting OSR-1 mRNA), and methods of using these compositions to impair deleterious nematodes.

6 Claims, 9 Drawing Sheets

Figure 3

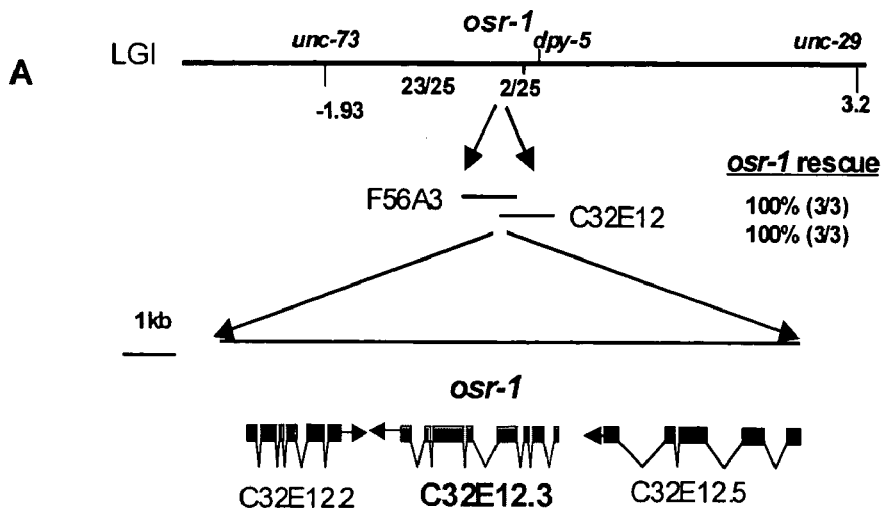

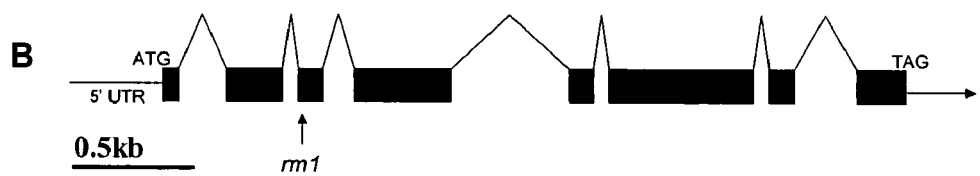

C  MILFLFLFLLLGFCIAPLSAQSPSTSDAPGALLSSLVGKSHQKLPLAPSME
ALELMGVQFVDALIKKGQMEMAKGAFKTQLEVLEKVHPDQFDKYKKLK
VDDLAADAVMQQAEMAKLQPKSGNAFIDMLNGNGIPIGSSIRGLEDAIRT
QRDMENTDPSEQIAKAVMDKFQTQILPGLVANMIAGKNPFKMPQQMRKA
QAAPSSVFQQALAQRAMLGKNAPVAGGRGEEQRMMMNRVDQRMQQRE
LQEEDEDDDDLEDEDVPRRRSSDGEPQSEAEHQRRDLARRLKSSPRLKEL
LQNAEVQSLLSYQRMRDSPLSKRRPLAMNDEDESAFRAMEARAKLDQKS
QLVLGLHGFGESDDDEDEEDENLIDPSENSFRRAPLRLSSGFVEKLKSNDE
LKSALDRIKYRVDDVEKYLAPKPMEFNPKPQPGYFAPRKIPTRPRKMLPLL
IGSDPKVQEEIRRHPSTEWKIAKESRVLTNLKNNPSLAALFMDDKLENTLK
GRQMLTDEQKGRTRVKTIRALPRLFGAPTAKAEMIDAKVFQDIEERPIPPLF
FEPKGRHTRLRWTGANEKEIPGLGSRFILPSLDPTMPALNTAFSTQGRARD
EWDTMFKIPNNWNPGDEVGFKMNSKTKRFVGGNGAFDMPALGL

Osr-1 sequence

```
atgattttattttttattttttattcctgttgttaggattttgtatcgcaccattatcggcccaatctccatcgacttccgatgctcc
gggagctttgttgtcatctctcgtaggtaaaagccatcaaaaactaccactggctccatcaatggaagctcttgaactga
tgggtgttcaatttgttgatgctctcatcaaaaaaggtcaaatggaaatggcaaaaggagcatttaagactcaattagaa
gttctagagaaagtacatcctgatcaattcgataagtacaaaaagctaaaagttgatgatttggcagctgatgcagttat
gcaacaggcggagatggcaaaattacagcctaaatcaggaaatgcatttatcgatatgttgaatggaaatggaatccc
aattggtagcagtattcgtggattagaagatgctatccgaacgcagagagatatggaaaatacggatccgtccgaaca
gattgccaaagccgtaatggacaaatttcaaacacaaattctcccaggactcgttgcaaatatgatcgctggcaagaa
ccccttaaaatgcctcaacaaatgagaaaagctcaagctgctccatcgtcagtgttccaacaagctcttgctcaaaga
gcaatgttaggtaaaaatgccccagttgccggtggaagaggtgaagaacaacggatgatgatgaatcgagtggacc
aaagaatgcaacaaagagaacttcaagaggaagatgaagatgatgatgatcttgaggacgaggatgtacccagaag
aagaagttcggatggagaaccacaaagtgaagcagagcatcagagaagagatttagccaggagattgaaaagtag
tcctagattaaaagagcttttacagaatgcggaagttcaatcattgctctcttaccaacgaatgagggattctccactga
gcaagcgaaggcctttggctatgaacgatgaggatgaaagtgcattccgcgcaatggaggctcgtgcaaaactaga
tcaaaaatctcaacttgtgctcggtctccatggttttggagagtctgatgatgatgaagacgaagaagatgaaaatttga
ttgatccatctgaaaattcattccgtcgtgcaccacttcgtctttcttccggattcgttgagaaattaaagtcaaatgatgaa
ttgaaaagtgcattggacagaattaaatatcgagttgatgacgtggaaaagtatcttgctccaaagccgatggaattca
atccaaaacctcagcctggctactttgctccacgtaaaatcccaacaagaccacgtaaaatgcttccattattaattgga
tctgatccaaaagttcaagaggaaatacgaagacatccaagtaccgaatggaaaattgcaaaagaatcaagagttttg
acaaatttgaagaataatccaagtcttgctgcattgttcatggatgataaattagagaatacattgaaaggaaggcaaat
gttaactgatgaacagaaaggtagaacacgtgtcaaaacaattcgtgcattaccaagactgttcggtgcaccaactgc
aaaagctgaaatgattgatgcaaaggtattccaagatattgaagaacgtcccattcctccattgttctttgaaccaaaag
gaaggcatacgagattgagatggactggagcaaatgaaaaagaaattccaggacttggaagtcgcttcattctcccat
ctcttgatccaactatgccagccttgaacacggctttctcgactcaggggcgagcccgtgacgagtgggataccatgt
tcaaaatcccgaataactggaatcctggagatgaagttgggttcaaaatgaactcaaaaaccaaacgattcgttggag
gaaatggagcatttgatatgcctgca ctgggattgtag
```

DAF-16 nucleotide

```
   1 ctcaaagcca atcaactcta ctcactttc ttcagaacct taacttttg tgtcactttc
  61 cccaaaaacc gttcaagctg ctgccttcac tctcatcccc tcctcttact ccttctttct
 121 cgtccgctac tactgtatct tctggacatc tacctgtata cacaccagtg gccagtcatc
 181 tgccattaca atttcatcaa ttgacacttc ttcaacaaca accgccgtcc tcattcactc
 241 ccgattcttc ctcatcctca acatcgtcgt ctttggctga aattcccgaa gacgttatga
 301 tggagatgct ggtagatcag ggaactgatg catcgtcatc cgcctccacg tccacctcat
 361 ctgtttcgag attcggagcg gacacgttca tgaatacacc ggatgatgtg atgatgaatg
 421 atgatatgga accgattcct cgtgatcggt gcaatacgtg gccaatgcgt aggccgcaac
 481 tcgaaccacc actcaactcg agtcccatta ttcatgaaca aattcctgaa gaagatgctg
 541 acctatacgg gagcaatgag caatgtggac agctcggcgg agcatcttca aacgggtcga
 601 cagcaatgct tcatactcca gatggaagca attctcatca gacatcgttt ccttcggaaa
 661 tgtccgaatc gccagacgat accgtatcgg gaaaaagac aacgaccaga cggaacgctt
 721 ggggaaatat gtcatatgct gaacttatca ctacagccat tatggctagt ccagagaaac
 781 ggttaactct tgcacaagtt tacgaatgga tggtccagaa tgttccatac ttcagggata
 841 agggagattc gaacagttca gctggatgga agaactcgat ccgtcacaat ctgtctcttc
 901 attctcgttt catgcgaatt cagaatgaag gagccggaaa gagctcgtgg tgggttatta
 961 atccagatgc aaagccagga aggaatccac ggcgtacacg tgaacgatcc aatactattg
1021 agacgactac aaaggctcaa ctcgaaaaat ctcgccgcgg agccaagaag aggataaagg
1081 agagagcatt gatgggctcc cttcactcga cacttaatgg aaattcgatt gccggatcga
1141 ttcaaacgat ttctcacgat ttgtatgatg atgattcaat gcaaggagca tttgataacg
1201 ttccatcatc tttccgtccc cgaactcaat cgaacctctc gattcctgga tcgtcgtctc
1261 gtgtttctcc agctattgga agtgatatct atgatgatct agaattccca tcatggggttg
1321 gcgaatcggt tccagcaatt ccaagtgata ttgttgatag aactgatcaa atgcgtatcg
1381 atgcaactac tcatattggt ggagttcaga ttaagcagga gtcgaagccg attaagacgg
1441 aaccaattgc tccaccacca tcataccacg agttgaacag tgtccgtgga tcgtgtgctc
1501 agaatccact tcttcgaaat ccaattgtgc caagcactaa cttcaagcca atgccactac
1561 cgggtgccta tggaaactat caaaatggtg gaataactcc aatcaattgg ctatcaacat
1621 ccaactcatc tccactgcct ggaattcaat cgtgtggaat tgtagctgca cagcatactg
1681 tcgcttcttc atcggctctt ccaattgatt tggaaaatct gacacttccc gatcagccac
1741 tgatggatac tatggatgtt gatgcattga tcagacatga gctgagtcaa gctggagggc
1801 agcatattca ttttgatttg taaattctct tcatttgtt tcccctggtg ttgttcgaaa
1861 gagagatagc aaagcagcga ggagtgagaa atcttccgtc ttcatctttt caaatcccta
1921 cctacacaca ctcaacgatc atcacagcca gaccatcaat atttcttccaa attttgacgt
1981 cgttaattt ttttcagttt tttcaaaaac tctattttct attttctgtc gtttgttccc
2041 cttctctcg tctaattcca acacattcat cccagtgacg tcgtgtaata ataatataaa
2101 atacctcttc tctctttctt cccctaatgc gaaatatcga aaaaccgttg attattacct
2161 cttttttctt gttttttttt tctctctctc tctcccgtca tccaggttct tcactcttta
2221 aatgctacct ctatcccatc ttttcgctg taaatttgtt tcgcaatcaa aactgctaaa
2281 acacattccc caatctgtct ttttaattg aattttcaa aaaatttgat ttcttgattt
2341 ctcttgtaat tctttaattt tcctcttttt tttccccctg gtagcaaatg tctagcgatt
2401 ctctttcttt ttttgtttaa ctttcacatc tggccgattc gaatcctccg tatacacaca
2461 cacatagtaa tctacctcca aaattttact gaaagatgtg atcccctctc tgtctccctc
2521 tacaaaacat tatttgtctg tttgtgtata ttgccaccac gtcgatttta aattaaaacc
2581 atcgtttttt cttcttttct actttttct cgaaaaattt aacaacacac aaaaaaatcc
2641 ttcaaaaaat ctcagtttta aatggtgtgg caatatatcg gatcccctc tacaccagaa
2701 cagtcttgca atttcagaga atgattttca gattttcat atcacaggcc cccttttttt
2761 gcttgttttt ttctctacct ctctttcttt tcattctatt tctctctctt gttttctctc
2821 tgttatcctg tacattttcc ttccaattct ttctggctat ttctgatttt cgagttcata
2881 ttctctacgt ctcacttct ctcgcgccac gccccctttt tcgtctccct ccgcccccaa
2941 atatatttgc gactgtatga tgatgatgat gatttaataa aaatcaaatt tga
```

FIGURE 7B

Daf-16 protein sequence

```
MNDSIDDDFP PEPRGRCYTW PMQQYIYQES SATIPHHHLN QHNNPYHPMH PHHQLPHMQQ
LPQPLLNLNM TTLTSSGSSV
ASSIGGGAQC SPCASGSSTA ATNSSQQQQT VGQMLAASVP CSSSGMTLGM SLNLSQGGGP
MPAKKKRCRK KPTDQLAQKK
PNPWGEESYS DIIAKALESA PDGRLKLNEI YQWFSDNIPY FGERSSPEEA AGWKNSIRHN
LSLHSRFMRI QNEGAGKSSW
WVINPDAKPG RNPRRTRERS NTIETTTKAQ LEKSRRGAKK RIKERALMGS LHSTLNGNSI
AGSIQTISHD LYDDDSMQGA
FDNVPSSFRP RTQSNLSIPG SSSRVSPAIG SDIYDDLEFP SWVGESVPAI PSDIVDRTDQ
MRIDATTHIG GVQIKQESKP
IKTEPIAPPP SYHELNSVRG SCAQNPLLRN PIVPSTNFKP MPLPGAYGNY QNGGITPINW
LSTSNSSPLP GIQSCGIVAA
QHTVASSSAL PIDLENLTLP DQPLMDTMDV DALIRHELSQ AGGQHIHFDL
```

Age-1 nucleotide sequence

```
   1 atgcatgtta acattttaca tccacaactg caaacgatgg tcgagcagtg gcaaatgcga
  61 gaacgcccat cgctggagac cgagaatggc aaaggatcgc tgctcctgga aatgaaggt
 121 gtcgcagata tcatcactat gtgtccattc ggagaagtta ttagtgtagt atttccgtgg
 181 tttcttgcaa atgtgcgaac atcgctagaa atcaagctat cagatttcaa acatcaactt
 241 ttcgaattga ttgctccgat gaagtgggga acatattccg taaagccaca ggattatgtg
 301 ttcagacagt tgaataattt cggcgaaatt gaagttatat ttaacgacga tcaaccoctg
 361 tcgaaattag agctccacgg cactttccca atgcttttc tctaccaacc tgatggaata
 421 aacagggata agaattaat gagtgatata agtcattgtc taggatactc actggataaa
 481 ctggaagaga gcctcgatga ggaactccgt caatttcgtg cttctctctg ggctcgtacg
 541 aagaaaacgt gcttgacacg tggacttgag ggtaccagtc actacgcgtt ccccgaagaa
 601 cagtacttgt gtgttggtga atcgtgcccg aaagatttgg aatcaaaagt caaggctgcc
 661 aagctgagtt atcagatgtt ttggagaaaa cgtaaagcgg aaatcaatgg agtttgcgag
 721 aaaatgatga agattcaaat tgaattcaat ccgaacgaaa ctccgaaatc tctgcttcac
 781 acgtttctct acgaaatgcg aaaattggat gtatacgata ccgatgatcc tgcagatgaa
 841 ggatggtttc ttcaattggc tggacgtacc acgtttgtta caaatccaga tgtcaaactt
 901 acgtcttatg atggtgtccg ttcggaactg gaaagctatc gatgccctgg attcgttgtt
 961 cgccgacaat cactagtcct caaagactat tgtcgcccaa aaccactcta cgaaccacat
1021 tatgtgagag cacacgaacg aaaacttgct ctagacgtgc tcagcgtgtc tatagatagc
1081 acaccaaaac agagcaagaa cagtgacatg gttatgactg attttcgtcc gacagcttca
1141 ctcaaacaag tttcactttg ggaccttgac gcgaatctta tgatacggcc tgtgaatatt
1201 tctggattcg atttcccggc cgacgtggat atgtacgttc gaatcgaatt cagtgtatat
1261 gtggggacac tgacgctggc atcaaaatct acaacaaaag tgaatgctca atttgcaaaa
1321 tggaataagg aaatgtacac tttgatcta tacatgaagg atatgccacc atctgcagta
1381 ctcagcattc gtgttttgta cggaaaagtg aaattaaaaa gtgaagaatt cgaagttggt
1441 tgggtaaata tgtccctaac cgattggaga gatgaactac gacaaggaca attttattc
1501 catctgtggg ctcctgaacc gactgccaat cgtagtagga tcggagaaaa tggagcaagg
1561 ataggcacca acgcagcggt tacaattgaa atctcaagtt atggtggtag agttcgaatg
1621 ccgagtcaag gacaataćac atatctcgtc aagcaccgaa gtacttggac ggaaactttg
1681 aatattatgg gtgatgacta tgagtcgtgt atcagagatc caggatataa gaagcttcag
1741 atgcttgtca agaagcatga atctggaatt gtattagagg aagatgaaca acgtcatgtc
1801 tggatgtgga ggagatacat tcaaaagcag gagcctgatt tgctcattgt gctctccgaa
1861 ctcgcatttg tgtggactga tcgtgagaac ttttccgagc tctatgtgat gcttgaaaaa
1921 tggaaaccgc cgagtgtggc agccgcgttg actttgcttg aaaacgttg cacggatcgt
1981 gtgattcgaa agtttgcagt ggagaagttg aatgagcagc tgagcccggt cacattccat
2041 ctttcatat tgcctctcat acaggcgttg aagtacgaac cgcgtgctca atcggaagtt
2101 ggaatgatgc tcttgactag agctctctgc gattatcgaa ttggacatcg acttttctgg
2161 ctgctccgtg cagagattgc tcgtttgaga gattgtgatc tgaaaagtga agaatatcgc
```

FIGURE 7C

```
2221 cgtatctcac ttctgatgga agcttacctc cgtggaaatg aagagcacat caagatcatc
2281 acccgacaag ttgacatggt tgatgagctc acacgaatca gcactcttgt caaaggaatg
2341 ccaaaagatg ttgctacgat gaaactgcgt gacgagcttc gatcgattag tcataaaatg
2401 gaaaatatgg attctccact ggatcctgtg tacaaactgg gtgaaatgat aatcgacaaa
2461 gccatcgtcc taggaagtgc aaaacgtccg ttaatgcttc actggaagaa caaaaatcca
2521 aagagtgacc tgcaccttcc gttctgtgca atgatcttca gaatggaga cgatcttcgc
2581 caggacatgc ttgttcttca agttctcgaa gttatggata acatctggaa ggctgcaaac
2641 attgattgct gtttgaaccc gtacgcagtt cttccaatgg gagaaatgat tggaattatt
2701 gaagttgtgc ctaattgtaa aacaatattc gagattcaag ttggaacagg attcatgaat
2761 acagcagttc ggagtattga tccttcgttt atgaataagt ggattcggaa acaatgcgga
2821 attgaagatg aaaagaagaa aagcaaaaag gactctacga aaaatcccat cgaaaagaag
2881 attgataata ctcaagccat gaagaaatat tttgaaagtg tcgatcgatt cctatactcg
2941 tgtgttggat attcagttgc cacgtacata atgggaatca aggatcgtca cagtgataat
3001 ctgatgctca ctgaagatgg aaaatatttc cacattgatt tcggtcacat tttgggacac
3061 ggaaagacca aacttggat ccagcgagat cgtcaaccgt ttattctaac cgaacacttt
3121 atgacagtga ttcgatcggg taaatctgtg gatggaaatt cgcatgagct acaaaaattc
3181 aaaacgttat gcgtcgaagc ctacgaagta atgtggaata atcgagattt gttcgtttcc
3241 ttgttcacct tgatgctcgg aatggagttg cctgagctgt cgacgaaagc ggatttggat
3301 catttgaaga aaaccctctt ctgcaatgga gaaagcaaag aagaagcgag aaagttttc
3361 gctggaatct acgaagaagc cttcaatgga tcatggtcta ccaaaacgaa ttggctcttc
3421 cacgcagtca aacactactg a
```

Age-1 protein sequence

```
MHVNILHPQL QTMVEQWQMR ERPSLETENG KGSLLLENEG VADIITMCPF GEVISVVFPW
FLANVRTSLE IKLSDFKHQL
FELIAPMKWG TYSVKPQDYV FRQLNNFGEI EVIFNDDQPL SKLELHGTFP MLFLYQPDGI
NRDKELMSDI SHCLGYSLDK
LEESLDEELR QFRASLWART KKTCLTRGLE GTSHYAFPEE QYLCVGESCP KDLESKVKAA
KLSYQMFWRK RKAEINGVCE
KMMKIQIEFN PNETPKSLLH TFLYEMRKLD VYDTDDPADE GWFLQLAGRT TFVTNPDVKL
TSYDGVRSEL ESYRCPGFVV
RRQSLVLKDY CRPKPLYEPH YVRAHERKLA LDVLSVSIDS TPKQSKNSDM VMTDFRPTAS
LKQVSLWDLD ANLMIRPVNI
SGFDFPADVD MYVRIEFSVY VGTLTLASKS TTKVNAQFAK WNKEMYTFDL YMKDMPPSAV
LSIRVLYGKV KLKSEEFEVG
WVNMSLTDWR DELRQGQFLF HLWAPEPTAN RSRIGENGAR IGTNAAVTIE ISSYGGRVRM
PSQGQYTYLV KHRSTWTETL
NIMGDDYESC IRDPGYKKLQ MLVKKHESGI VLEEDEQRHV WMWRRYIQKQ EPDLLIVLSE
LAFVWTDREN FSELYVMLEK
WKPPSVAAAL TLLGKRCTDR VIRKFAVEKL NEQLSPVTFH LFILPLIQAL KYEPRAQSEV
GMMLLTRALC DYRIGHRLFW
LLRAEIARLR DCDLKSEEYR RISLLMEAYL RGNEEHIKII TRQVDMVDEL TRISTLVKGM
PKDVATMKLR DELRSISHKM
ENMDSPLDPV YKLGEMIIDK AIVLGSAKRP LMLHWKNKNP KSDLHLPFCA MIFKNGDDLR
QDMLVLQVLE VMDNIWKAAN
IDCCLNPYAV LPMGEMIGII EVVPNCKTIF EIQVGTGFMN TAVRSIDPSF MNKWIRKQCG
IEDEKKKSKK DSTKNPIEKK
IDNTQAMKKY FESVDRFLYS CVGYSVATYI MGIKDRHSDN LMLTEDGKYF HIDFGHILGH
GKTKLGIQRD RQPFILTEHF
MTVIRSGKSV DGNSHELQKF KTLCVEAYEV MWNNRDLFVS LFTLMLGMEL PELSTKADLD
HLKKTLFCNG ESKEEARKFF
AGIYEEAFNG SWSTKTNWLF HAVKHY
```

OSR-1 NUCLEIC ACIDS AND PROTEINS

The present invention claims priority to U.S. Provisional Patent Application Ser. No. 60/433,819, filed on Dec. 16, 2002, herein incorporated by reference in its entirety.

The invention was made with government support under Grant No. 5r37gm038109 awarded by the NIGMS. The Government has certain rights in the invention.

FIELD OF THE INVENTION

The present invention relates to water-stress tolerance, in particular to the OSR-1 (osmotic stress resistant-1) protein, and nucleic acids encoding the OSR-1 protein. The present invention provides assays for the detection of OSR-1 gene and product, and for the detection of polymorphisms and mutations associated with water stress tolerance. The present invention also provides methods and compositions comprising small interfering RNA duplexes (RNAi), or vectors that encode dsRNA, that inhibit expression of the OSR-1 gene (e.g. by targeting OSR-1 mRNA), and methods of using these compositions to impair deleterious nematodes.

BACKGROUND OF THE INVENTION

Parasitic nematodes infect over half of the world's human population and also reduce agricultural productivity by more than US$100 billion annually. The most harmful human pathogens are *Ascaris lumbricoides, Ancylostoma duodenale, Necator americanus, Trichuris trichiura* and *Strongyloides stercoralis*. These pathogens infect more than 3 billion people causing malnutrition, obstructive intestinal disease and substantial morbidity particularly among school age children (~125,000 deaths each year) (Pearson, Current Infection Disease Report 4:59–64 (2002)). This will be aggravated in the future by lack of vaccines, limited chemical approaches, and the rapid increase in resistance to antihelmintic drugs (DeClercq et al., Am J Trop Med and Hygiene 57: 25–30 (1997), Hotez et al. Immunological Reviews 171: 163–171 (1999), Crompton, Adv. Parasitology 48: 285–375 (2001). Resistance to dehydration plays a key role in parasitic nematode epidemiology (Pit et al. Ann Trop Med Parasit 94: 165–171 (2000), Solomon et al. Parasitology 119: 621–626 (1999), Solomon et al. J Parasitology 84: 802–805 (1998), Solomon et al Int J Parasitology 27: 1517–1522 (1997)).

Contrary to human and animal parasitic nematodes, beneficial nematodes (*Steinernematidae* and *Heterorhabditidae*) are sensitive to dessication stress and other environmental constraints (Solomon et al., Nematology 1: 61–68 (1999), Kaya, Annual Review of Entomology 38: 181–206, (1993)). These nematodes are among the most promising alternatives to the chemical control of insect pests. They can actively locate, infect and kill a wide range of insect pest with the cooperation of a symbiotic bacterium (*Xenorhabdus* spp. and *Photorhabdus* spp.), and yet are safe for plants and animals.

Thus, there is a great need for understanding and modifying water stress tolerance of these and other organisms, for example, by decreasing water stress tolerance of pathogenic nematodes, and by increasing water stress tolerance of beneficial nematodes.

SUMMARY OF THE INVENTION

The present invention relates to water-stress tolerance, in particular to the OSR-1 (osmotic stress resistant-1) protein, and nucleic acids encoding the OSR-1 protein. The present invention provides assays for the detection of OSR-1 gene and product, and for the detection of polymorphisms and mutations associated with water stress tolerance. In particular, the present invention relates to compositions comprising small interfering RNA duplexes (RNAi), or vectors that encode dsRNA, that inhibit expression of the OSR-1 gene (e.g. by targeting OSR-1 mRNA), and methods of using these compositions to impair deleterious nematodes.

In some embodiments, the present invention provides a composition comprising an isolated collection of mutant (e.g., transgenic) nematodes altered to reduce or increase sensitivity to desiccation stress. In some embodiments, the mutant nematodes comprise a mutation that is a knock-out OSR-1 mutation. In some preferred embodiments, the collection of mutant nematodes is configured for administration to a host (e.g., a plant or animal).

The present invention also provides a method for treating a host organism, comprising the steps of exposing the host (e.g., plant or animal) to a collection of isolated mutant nematodes altered in sensitivity to desiccation stress as compared to non-mutant nematodes. In some embodiments, the mutant nematodes are altered to reduce sensitivity to desiccation stress. In some such embodiments, the nematodes comprise *Steinernematidae* or *Heterorhabditidae* nematodes. In other embodiments, the mutant nematodes are altered to increase sensitivity to desiccation stress.

The present invention also provides screening methods. For example, the present invention provides a method for screening for compounds that alter desiccation stress sensitivity in organisms, comprising the step of treating an organism with a test compound and detecting a change in OSR-1 expression in the organism in response to the test compound. In other embodiments, the present invention provides method for screening for compounds that alter desiccation stress sensitivity in organisms, comprising the step of exposing an OSR-1 polypeptide to a test compound and determining whether the test compound binds to the OSR-1 polypeptide or alters an activity of the OSR-1 polypeptide. In still further embodiments, the present invention provides a method for screening for compounds that alter desiccation stress sensitivity in organisms, comprising the step of exposing a cell to a test compound and detecting a change in OSR-1 expression in the cell in response to the test compound.

The present invention also provides novel nucleic acids and polypeptides and methods and kits employing the nucleic acids and polypeptides. Accordingly, in some embodiments, the present invention provides an isolated and purified nucleic acid comprising a sequence encoding an OSR-1 protein. In some embodiments, the sequence is operably linked to a heterologous promoter. In some embodiments, the sequence is contained within a vector. In some embodiments, the vector is within a host cell.

The present invention also provides an isolated and purified nucleic acid sequence that hybridizes under conditions of low stringency to a nucleic acid encoding an OSR-1 protein. In some embodiments, the sequence is contained within a vector. In some embodiments, the vector is in a host cell. In some embodiments, the host cell is located in an organism, wherein the organism is a non-human animal.

The present invention additionally provides a protein encoded by a nucleic acid selected from the group consisting of SEQ ID NOs: 1 and variants thereof that are at least 80% identical to SEQ ID NOs: 1. In some embodiments, the protein is encoded by a nucleic acid that is at least 90%, and preferably at least 95%, identical to SEQ ID NOs: 1. In some embodiments, the present invention provides a computer readable medium encoding a representation of the polypeptide sequence.

The present invention further provides a composition comprising a nucleic acid that inhibits the binding of at least a portion of a SEQ ID NO: 1 to its complementary sequence. In other embodiments, the present invention provides a polynucleotide sequence comprising at least fifteen nucleotides capable of hybridizing under stringent conditions to the isolated nucleotide sequence.

In yet other embodiments, the present invention provides a composition comprising a variant OSR-1 polypeptide, wherein the polypeptide comprises a C-terminal truncation of SEQ ID NO:2. In some embodiments, the presence of the variant polypeptide confers water stress tolerance.

In still further embodiments, the present invention provides a method for detection of a variant OSR-1 polypeptide in a subject, comprising: providing a biological sample from a subject, wherein the biological sample comprises an OSR-1 polypeptide; and detecting the presence or absence of a variant OSR-1 polypeptide in the biological sample. In some embodiments, the variant OSR-1 polypeptide is a polymorphism of SEQ ID NO: 2. In some embodiments, the presence of the variant OSR-1 polypeptide is indicative of water stress tolerance in the subject.

In some embodiments, the sample comprises a tissue sample, an egg sample, a larval sample, and a cyst sample. In some embodiments, the sample comprises an animal, animal waste product, food, water or soil. In some embodiments, the animal is a human or nematode. In some embodiments, the detecting comprises differential antibody binding. In other embodiments, the detection comprises a Western blot.

The present invention further provides a kit comprising a reagent for detecting the presence or absence of OSR-1 or a variant OSR-1 polypeptide in a biological sample. In some embodiments, the kit further comprises instruction for using the kit for detecting the presence or absence of a OSR-1 or a variant OSR-1 polypeptide in a biological sample. In some embodiments, the instructions comprise instructions required by the U.S. Food and Drug Agency for in vitro diagnostic kits.

In some embodiments, the reagent is one or more antibodies. In some embodiments, the antibodies comprise a first antibody that specifically binds to the C-terminus of the OSR-1 polypeptide and a second antibody that specifically binds to the N-terminus of the OSR-1 polypeptide.

In some embodiments, the present invention provides methods for inhibiting the expression of the OSR-1 gene comprising; a) provoding; i) a target cell expressing OSR-1 protein via expression of OSR-1 mRNA, and ii) a composition comprising a small interfering RNA duplex (RNAi), or vector encoding the dsRNA duplex, that targets the OSR-1 mRNA, and b) contacting the target cell with the composition such that the OSR-1 mRNA is disabled (e.g. cleaved), thereby inhibiting expression of the OSR-1 protein by the OSR-1 gene.

In certain embodiments, the target cell is a nematode cell. In other embodiments, the contacting is conducted in vitro. In particular embodiments the contacting is conducted under conditions such that said vector expresses said dsRNA in said target cell. In some embodiments, the composition further comprises a nucleic acid transfecting agent.

In certain embodiments, the present invention provides methods comprising; a) providing; i) a nematode, and ii) a composition comprising small interfering RNA duplexes (RNAi), or vector encoding the dsRNA, configured to inhibit expression of IOSR-1 protein, b) administering the composition to the nematode under conditions such that osmotic stress resistance in the nematode is reduced. In some embodiments, the present invention further comprises a nucleic acid transfecting agent. In preferred embodiments, the reagents of the present invention are suitable for field administration. In particularly preferred embodiments, reagents and compositions of the present invention contact target nematodes in the field.

In other embodiments, the present invention provides compositions comprising; a) a composition comprising small interfering RNA duplexes (RNAi), or vector encoding the dsRNA, configured to inhibit expression of OSR-1 protein, and b) a nucleic acid transfecting agent.

In some embodiments, the present invention provides kits comprising; a) a composition comprising small interfering RNA duplexes (RNAi), or vector encoding the dsRNA, configured to inhibit expression of OSR-1 protein, and b) printed material with instructions for employing the composition for treating a target cell expressing OSR-1 protein via expression of OSR-1 mRNA under conditions such that the OSR-1 mRNA is cleaved or otherwise disabled. In preferred embodiments, the target cell is a nematode cell.

In some embodiments, the modified animals, detection methods, screening methods and kits further employ, alone or in combination with OSR-1, one or more additional genes that influence water stress tolerance or other desired properties (e.g., oxidative stress resistance), including, but not limited to age-1 and daf-16 (See e.g., Honda and Honda, Ann. N.Y. Acad. Sci., 959:466 (2002)); and Murakami et al., Ann. N.Y. Acad. Sci., 908:40 (2000)). It is contemplated that Daf-16 sensitizes animals to desiccation stress and Age-1 promotes desiccation stress resistance.

DESCRIPTION OF THE FIGURES

FIG. 1A shows an N2 worm in isotonic medium (50 mM NaCl). FIGS. 1B–1D show dehydration of an N2 worm in osmotic stress during 10 minutes. FIGS. 1E–1G show recovery of a shrunken N2 worm in isotonic medium during 10 minutes. FIGS. 1H–1K show n osr-1 (rm1) worm in acute osmotic stress. FIG. 1L shows the time course of percent (%) motile N2 (open diamond), and osr-1(rm1) animals (solid square) in osmotic stress. The arrow indicates the time point when the inactive N2 worms were shifted to isotonic medium while osr-1(rm1) animals remained under the salt stress. The wild-type and osr-1(rm1) animals shown in this figure are of the same respective animal at different time points. The horizontal bar (FIG. 1K) equals 0.2 mm.

FIGS. 2A–2B show motility assays following acute and chronic exposure to 500 mM NaCl of wild-type (WT) (N2 strain) (diamond, and first bar of three) osr-1(rm1) (square, and second bar of three), and age-1(hx546) (triangle and third bar of three) animals at 1, 5 and 12 hours. FIG. 2C shows survival of N2 (diamond), osr-1(rm1) (square) and age-1(hx546) (triangle) animals during 3 days of exposure in 500 mM NaCl. FIG. 2D shows survival of N2 (diamond), osr-1(rm1) (square) and age-1 (hx546) (triangle) animals exposed to either heat-shock (35° C.), or in FIG. 2E, oxidative stress (300 mM paraquat). FIG. 2F shows an osmotic avoidance assay of N2/wild type (diamond), osr-1(rm1) (square), age-1(hx546) (triangle), osm-9(ky10) (open circle) and osm-10(n1052) (solid circle) animals. In each panel, error bars represent the standard error between 3–5 independent assays at each time point. Each assay contains 50–100 adult hermaphrodite animals tested.

FIG. 3 shows positional cloning of the OSR-1 gene. FIG. 3A shows genetic and physical maps of C. elegans chromosome I. OSR-1 maps to approximately −0.2 m.u. between two cloned genes UNC-73 and DPY-5. Numbers beneath the bar represent recombination events between DPY-5 and OSR-1 (2/25), and UNC-73 and OSR-1 (23/25). Numbers in parentheses show the fraction of transgenic lines that rescued osr-1(rm1) mutant animals. FIG. 3B shows the OSR-1 transcription unit. The full transcription unit of OSR-1 was determined using a partial EST (yk563c9) obtained from Yuji Kohara, and 5' RACE experiments. Since the OSR-1 mRNA does not have SL consensus splice sequences, a stop codon was introduced in the 5' untranslated region (UTR) immediately in frame with the first putative ATG site in the rescuing construct pASRM1. Injection of this construct into osr-1(rm1) mutant animals gave full rescue. FIG. 3C shows the amino acid sequence (SEQ ID NO:2) of the nematode OSR-1 protein of 643 amino acids with an N-terminal signal peptide (underlined).

FIG. 4A shows the L3 stage of N2 animals with expression of OSR-1 in the intestine and hypodermis. FIG. 4B shows a section from the mid-body of the L3 stage animal. Arrows indicate hypodermis (H) and intestine (I). FIG. 4C shows tissue-specific expression of OSR-1 in the hypodermis ($P_{dpy-7}$), intestine ($P_{vha-6}$), and nervous system ($P_{F25B3.3}$). Expression of OSR-1 cDNA under the hypodermal promoter was able to rescue all osr-1(rm1) phenotypes. Error bars represents standard errors between 3 trials for each behavioral and stress assays. In each trial >50 adult worms were analyzed.

FIG. 5 shows differential survival of N2, osr-1(rm1), sek-1 (km4), nsy-1(ky397), unc-43(n1186), daft16(mgdf50) and jnk-1(gk7) mutant animals in 500 mM NaCl. Progeny of each strain was grown on E. coli (HT115) carrying only the L4440 expression vector (solid bar) (control group), HT115 carrying the plasmid pDK177 (for PMK-1), or the plasmid pAS1 (for OSR-1), producing double-strand RNA (striped bar). On the x-axis, dark text indicates genetic background, while light text indicates the RNAi target gene. Error bars present the standard error between 3 replicates. Each replicate contained >250 adult hermaphrodite animals that were tested.

FIG. 6 shows the nucleic acid sequence (SEQ ID NO:1) of the nematode OSR-1 gene.

FIG. 7 shows the nucleic acid and amino acid sequences of Age-1 (SEQ ID NOS:5 and 6) and Daf-16 (SEQ ID NOS:3 and 4).

GENERAL DESCRIPTION OF THE INVENTION

Figure 1:
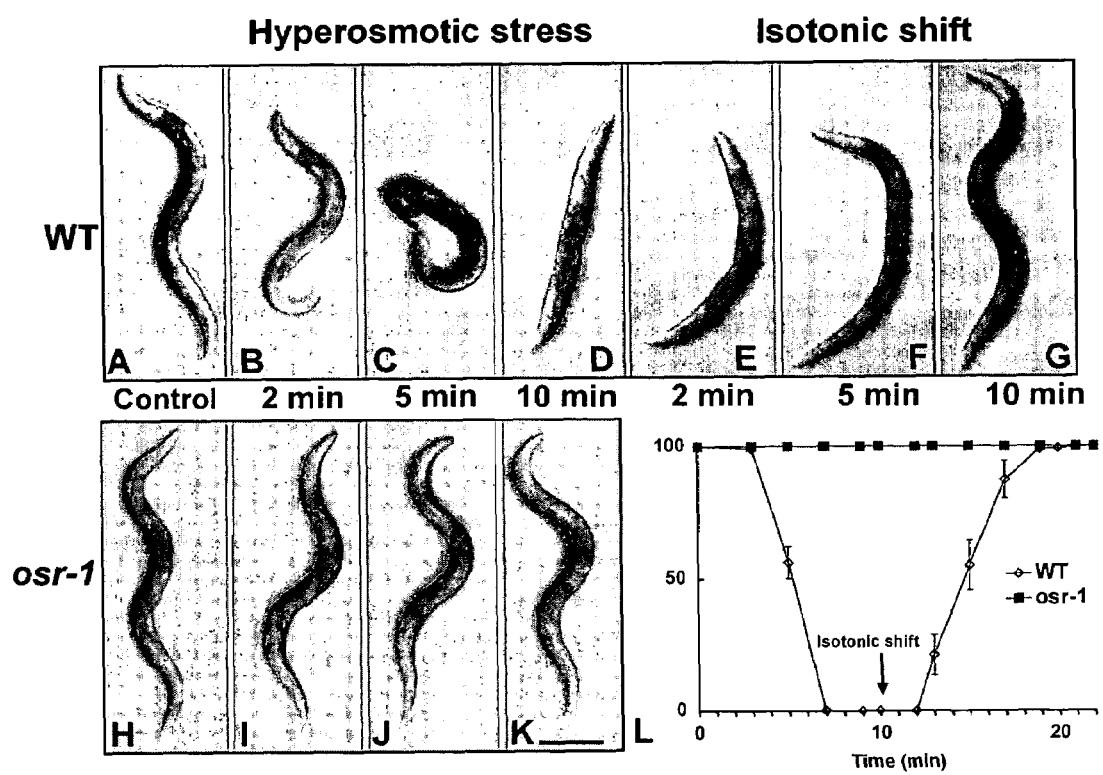
FIG. 1 shows characterization of the C. elegans osmotic stress response.

Infections with parasitic nematodes are most often acquired through ingestion of infective eggs and free-living larvae stages in contaminated food and water, or contact with infected soil. The resistance of the infective-stages to adverse environmental conditions (high salinity, drought and heat), in feces, soil and water is a key factor in parasitic nematode epidemiology (Pit et al. Ann Trop Med Parasit 94: 165–171 (2000), Solomon et al. Parasitology 119: 621–626 (1999), Solomon et al. J Parasitology 84: 802–805 (1998), Solomon et al Int J Parasitology 27: 1517–1522 (1997)). These environmental stages can survive in a dormant state in dry feces, or soil until they encounter a favorable condition for establishing a new infectious population (Perry, Parasitology 119: 19–30 (1999). This phenomenon is known as anhydrobiosis (caused by desiccation) or osmobiosis (caused by high salinity) (Womersley et al. Survival Biology. In: Free-living and plant parasitic nematodes. Perry R N, Wright D J, eds., 271–2989 (1998), Solomon et al. Nematology 1: 61–68 (1999)). For example A. lumbricoides eggs are long-lived and can survive for several years in dry or saline soil conditions (Feachem et al. Sanitation of disease: Health aspects of Excreta and wastewater management (1983).

Wild-type C. elegans worms detect and avoid hyperosmotic environments, and mutants defective in sensing high osmolarity (OSM) have been described (Colbert et al., J Neruosci 17: 8259–8269 (1997), Culotti et al., Genetics 90: 243–256 (1978), Hart et al., J Neurosci 19: 1952–1958 (1999)). Unlike wild-type animals, osm mutants fail to avoid environments of high osmolarity, at least partly due to defective function of the polymodal osmosensory ASH neurons (Colbert et al., J Neurosci 17: 8259–8269 (1997), Hart et al., J Neurosci 19: 1952–1958 (1999)).

Experiments conducted during the course of the development of the present invention have characterized a novel protein, OSR-1, in C. elegans and identified and cloned a distinct gene, OSR-1, that causes a striking dehydration resistance phenotype under hyperosmotic stress conditions. OSR-1(rm1) is a novel gene with a domain associated with sensory signaling in a two-component system (Perry, Parasitology 119: 19–30 (1999)). The present invention is not limited to a particular mechanism of action. Indeed, an understanding of the mechanism is not necessary to practice the invention. Nonetheless, it contemplated that OSR-1 is a key constituent of a two-component signal transduction pathway. Two-component signal transduction systems play a prominent role in the response of prokaryotes and eukaryotes to the extracellular environment and are composed of a sensor and a response regulator. Protein sequence analysis of OSR-1 has identified a short segment of similarity between OSR-1 and the receiver domain of the response regulator, Ssk1; a member of the osmo-sensing two-component system in the budding yeast, Saccharomyces cerevisiae. Detection of the environmental cues (such as high osmolarity in yeast) by the sensor molecule causes the inhibition of a phosphorylation system resulting in dephosphorylation of a conserved aspartate residue in the receiver domain containing protein, Ssk1. In the budding yeast, this leads to the activation of the HOG/MAP Kinase cascade and downstream glycerol synthesis, the latter being crucial for hyperosmolarity adaptation (Posas, 1996). A receiver-like domain with the conserved aspartate (D489) is located in the C-terminal region of OSR-1. Consistent with the notion that OSR-1 is a response regulator, is the finding that OSR-1 mutants have high levels of glycerol. Thus the present invention provides a novel gene with a critical role to play in the response of organisms to the extracellular environment.

Definitions

To facilitate understanding of the invention, a number of terms are defined below.

As used herein, the term "OSR-1" or "osmotic stress resistant-1" when used in reference to a protein or nucleic acid refers to a protein or nucleic acid encoding a protein that, in some forms, is correlated with water stress tolerance. The term OSR-1 encompasses both protein represented by SEQ ID NO:2, as well as variants or chimeric genes constructed with portions of OSR-1 coding regions that have the biological properties of OSR-1.

As used herein, the term "instructions for using said kit for said detecting the presence or absence of OSR-1 in a said biological sample" includes instructions for using the reagents contained in the kit for the detection of variant and wild type OSR-1 nucleic acids or polypeptides.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., OSR-1). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "transfection" as used herein refers to the introduction of foreign DNA or RNA into eukaryotic cells. Transfection may be accomplished by a variety of means known to the art including calcium phosphate-DNA co-precipitation, DEAE-dextran-mediated transfection, OLIGOFECTAMINE, polybrene-mediated transfection, In particular, the term "OSR-1 gene" refers to the full-length OSR-1 nucleotide sequence (e.g., contained in SEQ ID NO: 1). However, it is also intended that the term encompass mutants as well as other domains within the full-length OSR-1 nucleotide sequence. Furthermore, the terms "OSR-1 nucleotide sequence" or "OSR-1 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional-properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant understands that stringency conditions may be altered for probes of other sizes (See e.g., Anderson and Young, Quantitative Filter Hybridization, in Nucleic Acid Hybridization [1985] and Sambrook et al., Molecular Cloning: A Laboratory Manual, Cold Spring Harbor Press, NY (1989)).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., OSR-1).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the OSR-1 gene).

As used herein, the term "detection assay" refers to an assay for detecting the presence of absence of variant nucleic acid sequences (e.g., polymorphism or mutations) in a given allele of a particular gene (e.g., the OSR-1 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 (1972)). Other nucleic acid will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4: (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the MRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding OSR-1 includes, by way of example, such nucleic acid in cells ordinarily expressing OSR-1 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, OSR-1 antibodies are purified by removal of contaminating non-immunoglobulin proteins; they are also purified by the removal of immunoglobulin that does not bind OSR-1. The removal of non-immunoglobulin proteins and/or the removal of immunoglobulins that do not bind OSR-1 results in an increase in the percent of OSR-1-reactive immunoglobulins in the sample. In another example, recombinant OSR-1 polypeptides are expressed in bacterial host cells and the polypeptides are purified by the removal of host cell proteins; the percent of recombinant OSR-1 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of a nematode by experimental manipulations and may include gene sequences found in that nematode so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of MRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced OSR-1 transgene RNA is quantified; other minor species of RNA which hybridize to the transgene probe are not considered in the quantification of the expression of the transgenic mRNA.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a chromosome or sequences associated with a chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DETAILED DESCRIPTION OF THE INVENTION

The present invention relates to water-stress tolerance, in particular to the OSR-1 (osmotic stress resistant-1) protein, and nucleic acids encoding the OSR-1 protein. The present invention provides assays for the detection of OSR-1, and polymorphisms and mutations associated with water stress tolerance. In particular, the present invention relates to compositions comprising small interfering RNA duplexes (RNAi), or vectors that encode dsRNA, that inhibit expression of the OSR-1 gene (e.g. by targeting OSR-1 MRNA), and methods of using these compositions to impair deleterious nematodes.

I. OSR-1 Polynucleotides

As described above, a new gene associated with water stress tolerance has been discovered. Accordingly, the present invention provides nucleic acids encoding OSR-1 genes, homologs, variants (e.g., polymorphisms and mutants), including but not limited to, those described in SEQ ID NO: 1. In some embodiments, the present invention provide polynucleotide sequences that are capable of hybridizing to SEQ ID NO: 1 under conditions of low to high stringency as long as the polynucleotide sequence capable of hybridizing encodes a protein that retains a biological activity of the naturally occurring OSR-1. In some embodiments, the protein that retains a biological activity of naturally occurring OSR-1 is 70% homologous to wild-type OSR-1, preferably 80% homologous to wild-type OSR-1, more preferably 90% homologous to wild-type OSR-1, and most preferably 95% homologous to wild-type OSR-1. In preferred embodiments, hybridization conditions are based on the melting temperature ($T_m$) of the nucleic acid binding complex and confer a defined "stringency" as explained above (See e.g., Wahl, et al., Meth. Enzymol., 152:399–407 (1987), incorporated herein by reference).

In other embodiments of the present invention, additional alleles of OSR-1 are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter an OSR-1 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of OSR-1 may be extended utilizing the nucleotide sequence (e.g., SEQ ID NO: 1) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318–22 (1993)). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 (1988)). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055–60 (1991)). The PROMOT-ERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include nematode libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic nematode libraries are useful for obtaining introns and extending 5' sequence.

In other embodiments of the present invention, variant(s) of the disclosed OSR-1 sequences are provided. In preferred embodiments, variant(s) result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., OSR-1 function) for such purposes as altering the biological activity (e.g., prevention or enhancement of water stress tolerance). Such modified peptides are considered functional equivalents of peptides having an activity of OSR-1 as defined herein. A modified peptide can be produced in which the nucleotide sequence encoding the polypeptide has been altered, such as by substitution, deletion, or addition. In particularly preferred embodiments, these modifications do not significantly reduce the biological activity of the modified OSR-1. In other words, construct "X" can be evaluated in order to determine whether it is a member of the genus of modified or variant OSR-1's of the present invention as defined functionally, rather than structurally. In preferred embodiments, the activity of variant OSR-1 polypeptides is evaluated by methods described herein (e.g., the generation of transgenic nematodes).

Moreover, as described above, variant forms of OSR-1 are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of OSR-1 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, WH Freeman and Co., (1981)). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a OSR-1 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. OSR-1 Polypeptides

In other embodiments, the present invention provides OSR-1 polynucleotide sequences that encode OSR-1 polypeptide sequences. OSR-1 polypeptides (e.g., SEQ ID NO:2) are described in FIG. 3C. Other embodiments of the present invention provide fragments, fusion proteins or functional equivalents of these OSR-1 proteins. In some embodiments, the present invention provides mutants of OSR-1. In still other embodiment of the present invention, nucleic acid sequences corresponding to OSR-1 variants, homologs, and mutants may be used to generate recombinant DNA molecules that direct the expression of the OSR-1 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO: 1 that encode substantially the same or a functionally equivalent amino acid sequence, may be used to clone and express OSR-1. In general, such polynucleotide sequences hybridize to SEQ ID NO: 1 under conditions of high to medium stringency as described above. As will be understood by those of skill in the art, it may be advantageous to produce OSR-1-encoding nucleotide sequences possessing non-naturally occurring codons. Therefore, in some preferred embodiments, codons preferred by a particular prokaryotic or eukaryotic host (Murray et al., Nucl. Acids Res., 17 (1989)) are selected, for example, to increase the rate of OSR-1 expression or to produce recombinant RNA transcripts having desirable properties, such as a longer half-life, than transcripts produced from naturally occurring sequence.

A. Vectors for Production of OSR-1

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above. In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO: 1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, pXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by organisms is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of OSR-1

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli*, *Salmonella typhimurium*, *Bacillus subtilis*, and various species within the genera *Pseudomonas*, *Streptomyces*, and *Staphylococcus*, as well as *Saccharomycees cerivisiae*, *Schizosaccharomycees pombe*, *Drosophila* S2 cells, *Spodoptera* Sf9 cells, Chinese hamster ovary (CHO) cells, COS-7 lines of monkey kidney fibroblasts, (Gluzman, Cell 23:175 (1981)), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, (1986)). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

C. Purification of OSR-1

The present invention also provides methods for recovering and purifying OSR-1 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NO:1) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 (1984)).

D. Mutants of OSR-1

In addition, the present invention provides sequence(s) of OSR-1 mutants. In some embodiments of the present invention, when expression of a portion of the OSR-1 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al., J. Bacteriol., 169:751 (1987)) and Salmonella typhimurium and its in vitro activity has been demonstrated on recombinant proteins (Miller et al., Proc. Natl. Acad. Sci. USA 84:2718 (1990)). Therefore, removal of an N-terminal methionine, if desired, can be achieved either in vivo by expressing such recombinant polypeptides in a host which produces MAP (e.g., E. coli or CM89 or S. cerivisiae), or in vitro by use of purified MAP.

E. Fusion Proteins Containing OSR-1

The present invention also provides fusion proteins incorporating all or part of OSR-1. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of an OSR-1 protein. In some embodiments of the present invention, the VP6 capsid protein of rotavirus is used as an immunologic carrier protein for portions of the OSR-1 polypeptide, either in the monomeric form or in the form of a viral particle. In other embodiments of the present invention, the nucleic acid sequences corresponding to the portion of OSR-1 against which antibodies are to be raised can be incorporated into a fusion gene construct which includes coding sequences for a late vaccinia virus structural protein to produce a set of recombinant viruses expressing fusion proteins comprising a portion of OSR-1 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of OSR-1 and the poliovirus capsid protein are created to enhance immunogenicity of the set of polypeptide antigens (See e.g., EP Publication No. 025949; and Evans et al., Nature 339:385 (1989); Huang et al., J. Virol., 62:3855 (1988); and Schlienger et al., J. Virol., 66: (1992)).

In still other embodiments of the present invention, the multiple antigen peptide system for peptide-based immunization can be utilized. In this system, a desired portion of OSR-1 is obtained directly from organo-chemical synthesis of the peptide onto an oligomeric branching lysine core (see e.g., Posnett et al., J. Biol. Chem., 263:1719 (1988); and Nardelli et al., J. Immunol., 148:914 (1992)). In other embodiments of the present invention, antigenic determinants of the OSR-1 proteins can also be expressed and presented by bacterial cells.

In addition to utilizing fusion proteins to enhance immunogenicity, it is widely appreciated that fusion proteins can also facilitate the expression of proteins, such as the OSR-1 protein of the present invention. Accordingly, in some embodiments of the present invention, OSR-1 can be generated as a glutathione-S-transferase (i.e., GST fusion protein). It is contemplated that such GST fusion proteins will enable easy purification of OSR-1, such as by the use of glutathione-derivatized matrices (See e.g., Ausabel et al. (eds.), Current Protocols in Molecular Biology, John Wiley & Sons, NY (1991)). In another embodiment of the present invention, a fusion gene coding for a purification leader sequence, such as a poly-(His)/enterokinase cleavage site sequence at the N-terminus of the desired portion of OSR-1, can allow purification of the expressed OSR-1 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 (1987); and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

F. Variants of OSR-1

Still other embodiments of the present invention provide mutant or variant forms of OSR-1 (i.e., muteins). It is possible to modify the structure of a peptide having an activity of OSR-1 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject OSR-1 proteins as defined herein. A modified peptide can be produced in which the amino acid sequence has been altered, such as by amino acid substitution, deletion, or addition.

Moreover, as described above, variant forms (e.g., mutants or polymorphic sequences) of the subject OSR-1 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present OSR-1 proteins, and is especially useful for identifying potential variant sequences (i.e., mutants or polymorphic sequences) that are involved in water stress tolerance. The purpose of screening such combinatorial libraries is to generate, for example, novel OSR-1 variants that can act as either agonists or antagonists, or alternatively, possess novel activities all together.

Therefore, in some embodiments of the present invention, OSR-1 variants are engineered by the present method to provide altered (e.g., increased or decreased) biological activity. In other embodiments of the present invention, combinatorially-derived variants are generated which have a selective potency relative to a naturally occurring OSR-1. Such proteins, when expressed from recombinant DNA constructs, can be used in gene transfer protocols.

Still other embodiments of the present invention provide OSR-1 variants that have intracellular half-lives dramatically different than the corresponding wild-type protein. For example, the altered protein can be rendered either more stable or less stable to proteolytic degradation or other cellular process that result in destruction of, or otherwise inactivate OSR-1. Such variants, and the genes which encode them, can be utilized to alter the location of OSR-1 expression by modulating the half-life of the protein. For instance, a short half-life can give rise to more transient OSR-1 biological effects and, when part of an inducible expression system, can allow tighter control of OSR-1 levels within the cell. As above, such proteins, and particularly their recombinant nucleic acid constructs, can be used in gene transfer protocols.

In still other embodiments of the present invention, OSR-1 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of OSR-1 homologs, variants or other related proteins are aligned, preferably to promote the highest homology possible. Such a population of variants can include, for example, OSR-1 homologs from one or more species, or OSR-1 variants from the same species but which differ due to mutation or polymorphisms. Amino acids that appear at each position of the aligned sequences are selected to create a degenerate set of combinatorial sequences.

In a preferred embodiment of the present invention, the combinatorial OSR-1 library is produced by way of a degenerate library of genes encoding a library of polypeptides which each include at least a portion of potential OSR-1 protein sequences. For example, a mixture of synthetic oligonucleotides can be enzymatically ligated into gene sequences such that the degenerate set of potential OSR-1 sequences are expressible as individual polypeptides, or alternatively, as a set of larger fusion proteins (e.g., for phage display) containing the set of OSR-1 sequences therein.

There are many ways by which the library of potential OSR-1 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential OSR-1 sequences. The synthesis of degenerate oligonucleotides is well known in the art (See e.g., Narang, Tetrahedron Lett., 39:39 (1983); Itakura et al., Recombinant DNA, in Walton (ed.), *Proceedings of the 3rd Cleveland Symposium on Macromolecules*, Elsevier, Amsterdam, pp 273–289 (1981); Itakura et al., Annu. Rev. Biochem., 53:323 (1984); Itakura et al., Science 198:1056 (1984); Ike et al., Nucl. Acid Res., 11:477 (1983)). Such techniques have been employed in the directed evolution of other proteins (See e.g., Scott et al., Science 249:386 (1980); Roberts et al., Proc. Natl. Acad. Sci. USA 89:2429 (1992); Devlin et al., Science 249: 404 (1990); Cwirla et al., Proc. Natl. Acad. Sci. USA 87: 6378 (1990); each of which is herein incorporated by reference; as well as U.S. Pat. Nos. 5,223,409, 5,198,346, and 5,096,815; each of which is incorporated herein by reference).

It is contemplated that the OSR-1 nucleic acids (e.g., SEQ ID NO:1, and fragments and variants thereof) can be utilized as starting nucleic acids for directed evolution. These techniques can be utilized to develop OSR-1 variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 (1996); Leung et al., Technique, 1:11 (1989); Eckert and Kunkel, PCR Methods Appl., 1:17–24 (1991); Caldwell and Joyce, PCR Methods Appl., 2:28 (1992); and Zhao and Arnold, Nuc. Acids. Res., 25:1307 (1997)). After mutagenesis, the resulting clones are selected for desirable activity (e.g., screened for OSR-1 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 (1994); U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full-length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 (1994); Stemmer, Proc. Natl. Acad. Sci. USA, 91:10747 (1994); Crameri et al., Nat. Biotech., 14:315 (1996); Zhang et al., Proc. Natl. Acad. Sci.

USA, 94:4504 (1997); and Crameri et al., Nat. Biotech., 15:436 (1997)). Variants produced by directed evolution can be screened for OSR-1 activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of OSR-1 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

G. Chemical Synthesis of OSR-1

In an alternate embodiment of the invention, the coding sequence of OSR-1 is synthesized, whole or in part, using chemical methods well known in the art (See e.g., Caruthers et al., Nucl. Acids Res. Symp. Ser., 7:215 (1980), Crea and Horn, Nucl. Acids Res., 9:2331 (1980), Matteucci and Caruthers, Tetrahedron Lett., 21:719 (1980), and Chow and Kempe, Nucl. Acids Res., 9:2807 (1981)). In other embodiments of the present invention, the protein itself is produced using chemical methods to synthesize either an entire OSR-1 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. (1983)). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 (1995)) and automated synthesis may be achieved, for example, using ABI 431A Peptide Synthesizer (Perkin Elmer) in accordance with the instructions provided by the manufacturer. Additionally, the amino acid sequence of OSR-1, or any part thereof, may be altered during direct synthesis and/or combined using chemical methods with other sequences to produce a variant polypeptide.

III. Detection of OSR-1 Alleles

In some embodiments, the present invention provides methods of detecting the presence of OSR-1 nucleic acids or polypeptides. The detection of mutant OSR-1 polypeptides finds use in the identification of water stress tolerant and intolerant nematodes.

A. OSR-1 Alleles

In some embodiments, the present invention includes alleles of OSR-1 that increase a pathogenic nematode's sensitivity to water stress, or decrease a beneficial nematodes sensitivity to water stress. Any mutation that results in the desired phenotype (e.g., increased or decreased water stress tolerance OSR-1) is within the scope of the present invention.

B. Detection of OSR-1 Alleles

Accordingly, the present invention provides methods for determining whether a nematode has an increased or decreased susceptibility to water stress by determining whether the nematode species, strain or individual has a variant OSR-1 allele. A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct Sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of OSR-1 (e.g., to the region of polymorphism or mutation). Both sets of primers are used to amplify a sample of DNA. If only the mutant primers result in a PCR product, then the subject nematode has the mutant OSR-1 allele. If only the wild-type primers result in a PCR product, then the subject has the wild type allele of OSR-1.

3. Mutational Detection by dHPLC

In some embodiments of the present invention, variant sequences are detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

4. Fragment Length Polymorphism Assays

In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

5. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY (1991)). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or non-specifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717; 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLI-TAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

6. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the Spectro-READER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3–5 second including repetitive data collection. The SpectroTYPER software then calculates, records, compares and reports the genotypes at the rate of three seconds per sample.

7. Detection of Variant OSR-1 Proteins

In other embodiments, variant OSR-1 polypeptides are detected. Any suitable method may be used to detect mutant OSR-1 polypeptides including, but not limited to, those described below.

a) Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a TSC1 or TSC2 protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

b) Antibody Binding

In still further embodiments of the present invention, antibodies (See below for antibody production) are used to determine if an individual subject contains an allele encoding a variant OSR-1 gene. In preferred embodiments, antibodies are utilized that discriminate between variant and wild-type proteins (SEQ ID NO: 2). In some particularly preferred embodiments, antibodies differentially bind to wild type or variant forms of OSR-1.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference.

8. Kits for Analyzing Water Stress Tolerance

The present invention also provides kits for determining whether an individual subject contains an allele of OSR-1. In some embodiments, the kits are useful determining whether the subject is sensitive or resistant to water stress. The diagnostic kits are produced in a variety of ways. In some embodiments, the kits contain at least one reagent for specifically detecting a mutant OSR-1 allele or protein. In preferred embodiments, the kits contain reagents for detecting a mutation in the OSR-1 gene. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated OSR-1 proteins.

In some embodiments, the kit contains instructions for determining whether the subject is susceptible or resistant to water stress. In preferred embodiments, the instructions specify that risk for water stress sensitivity or resistance is determined by detecting the presence or absence of a mutant OSR-1 allele in the subject, wherein subjects having a mutant allele are at greater or lesser risk for water stress.

The presence of absence of a water stress tolerance gene can be used to make therapeutic or other critical decisions. For example, beneficial nematodes with mutant OSR-1 alleles conferring enhanced water stress tolerance may be preferred for long-lasting insecticidal capacity after application, whereas reinfection rates with pathogenic nematodes expressing decreased water stress tolerance are likely to be reduced.

In some embodiments, the kits include ancillary reagents such as buffering agents, nucleic acid stabilizing reagents, protein stabilizing reagents, and signal producing systems (e.g., florescence generating systems as FRET systems). The test kit may be packages in any suitable manner, typically with the elements in a single container or various containers as necessary along with a sheet of instructions for carrying out the test. In some embodiments, the kits also preferably include a positive control sample.

IV. Generation of OSR-1 Antibodies

The present invention provides isolated antibodies or antibody fragments (e.g., FAB fragments). Antibodies can be generated to allow for the detection of OSR-1 protein. The antibodies may be prepared using various immunogens. In one embodiment, the immunogen is a nematode OSR-1 peptide to generate antibodies that recognize nematode OSR-1. Such antibodies include, but are not limited to, polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against OSR-1. For the production of antibody, various host animals can be immunized by injection with the peptide corresponding to the OSR-1 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward OSR-1, it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495–497 (1975)), as well as the trioma technique, the human B-cell hybridoma technique (See e.g., Kozbor et al., Immunol. Tod., 4:72 (1983)), and the EBV-hybridoma technique to produce human monoclonal antibodies (Cole et al., in *Monoclonal Antibodies and Cancer Therapy*, Alan R. Liss, Inc., pp. 77–96 (1985)).

In an additional embodiment of the invention, monoclonal antibodies are produced in germ-free animals utilizing technology such as that described in PCT/US90/02545).

In addition, it is contemplated that techniques described for the production of single chain antibodies (U.S. Pat. No. 4,946,778; herein incorporated by reference) will find use in producing OSR-1 specific single chain antibodies. An additional embodiment of the invention utilizes the techniques described for the construction of Fab expression libraries (Huse et al., Science 246:1275–1281 (1989)) to allow rapid and easy identification of monoclonal Fab fragments with the desired specificity for OSR-1.

In other embodiments, the present invention contemplated recombinant antibodies or fragments thereof to the proteins of the present invention. Recombinant antibodies include, but are not limited to, chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffuision precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of OSR-1 (e.g., for Western blotting), measuring levels thereof in appropriate biological samples, etc. The antibodies can be used to detect OSR-1 in a biological sample from an individual subject. The biological sample can be a biological fluid, such as, but not limited to, blood, serum, plasma, urine, cerebrospinal fluid, and the like, or non-biological sample (e.g. water, food, soil) containing adult, larval, cyst or egg nematodal forms.

The biological samples can then be tested directly for the presence of nematode OSR-1 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of OSR-1 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of OSR-1 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of OSR-1.

V. Transgenic and Mutant Animals Expressing Exogenous OSR-1 Genes and Homologs, Mutants, and Variants Thereof

A. Transgenic and Mutant Nematodes

The present invention contemplates the generation of transgenic animals (e.g., nematodes) comprising an exogenous OSR-1 gene or homologs, mutants, or variants thereof. In other embodiments, the present invention provides collections of natural mutants (e.g., identified using the methods described above). In preferred embodiments, the transgenic or mutant nematode displays an altered phenotype as compared to wild-type animals. In some embodiments, the altered phenotype is the overexpression of mRNA for an OSR-1 gene as compared to natural levels of OSR-1 expression. In other embodiments, the altered phenotype is the decreased expression of mRNA for an endogenous OSR-1 gene as compared to natural levels of endogenous OSR-1 expression. In some preferred embodiments, the transgenic or mutant animals comprise mutant alleles of OSR-1 conferring enhanced or suppressed water stress tolerance. Methods for analyzing the presence or absence of such phenotypes include Northern blotting, mRNA protection assays, and RT-PCR. In other embodiments, the transgenic or mutant nermatodes have a knock-out of the OSR-1 gene. In preferred embodiments, the transgenic or mutant animals display a water stress tolerance-associate phenotype.

Such nematodes find use in research applications (e.g., identifying signaling pathways that OSR-1 is involved in), as well as reagent screening applications (e.g., to screen for drugs that promote or inhibit OSR-1 expression). For example, in some embodiments, test compounds (e.g., a drug that is suspected of being useful to alter water stress tolerance) and control compounds (e.g., a placebo) are administered to the transgenic or mutant nematodes and the control nematodes and the effects evaluated. The effects of the test and control compounds on the water stress phenotype are then assessed.

The transgenic or mutant nematodes also find use in at therapeutic or agriculturally beneficial organisms. In some embodiments, collections of the transgenic or mutant nematodes are assembled and provided to a host organism (e.g., to displace pathogenic versions) or sprayed or otherwise administered to plants or in agricultural settings (e.g., to reduce the abundance of pests).

In some embodiments, the modified animals, detection methods, screening methods and kits further employ, alone or in combination with OSR-1, one or more additional genes that influence water stress tolerance or other desired properties (e.g., oxidative stress resistance), including, but not limited to age-1 and daf-16 (See e.g., Honda and Honda, Ann. N.Y. Acad. Sci., 959:466 (2002)); and Murakami et al., Ann. N.Y. Acad. Sci., 908:40 (2000)). It is contemplated that Daf-16 sensitizes animals to desiccation stress and Age-1 promotes desiccation stress resistance.

The transgenic or mutant nematodes can be generated via a variety of methods. Nucleic acid containing the transgene can be directly microinjected into the nematodes. Co-integrations markers may be used to help identify integrated animals.

In still other embodiments, homologous recombination is utilized to knock-out gene function or create deletion mutants (e.g., mutants in which the LTRs of OSR-1 are deleted). Methods for homologous recombination are described in U.S. Pat. No. 5,614,396, incorporated herein by reference.

B. RNA Interference (RNAi)

The present invention provides RNAi for inhibiting the expression of the OSR-1 protein in cells. Preferably, inhibition of the level of Osr-1 expression in cells prevents or reduces the capacity for osmotic resistance in nematodes. RNAi represents an evolutionary conserved cellular defense for controlling the expression of foreign genes in most eukaryotes. RNAi is triggered by double-stranded RNA (dsRNA) and causes sequence-specific mRNA degradation of single-stranded target RNAs homologous in response to dsRNA. The mediators of mRNA degradation are small interfering RNA duplexes (RNAi), which are normally produced from long dsRNA by enzymatic cleavage in the cell. RNAi are generally approximately twenty-one nucleotides in length (e.g. 21–23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21–23 nt dsRNA fragments.

Chemically synthesized dsRNAs have become powerful reagents for genome-wide analysis of gene function in cultured somatic cells. The transfection of dsRNAs into host cells results in the potent, long-lasting post-transcriptional silencing of specific genes (Caplen et al, Proc Natl Acad Sci U.S.A. 98: 9742–7 (2001), Elbashir et al., Nature 2001 411:494–8 (2001), Elbashir et al., Genes Dev 15: 188–200 (2001), and Elbashir et al., EMBO J. 20: 6877–88 (2001)). Methods and compositions for performing RNAi with dsRNAs are described, for example, in U.S. Pat. No. 6,506,559. RNAi is extraordinarily effective at lowering the amounts of targeted RNA, and by extension proteins, frequently to undetectable levels. The silencing effect can last several months, and is extraordinarily specific, because one nucleotide mismatch between the target RNA and the central region of the dsRNA is frequently sufficient to prevent silencing (Brummelkamp et al, Science 296:550–3 (2002), and Holen et al, Nucleic Acids Res. 30:1757–66 (2002).

1. Designing and Testing RNAi for OSR-1

In order to design dsRNAs for OSR-1 (e.g. that target OSR-1 mRNA) software design tools are available in the art (e.g. on the Internet). For example, Oligoengine's web page has one such design tool that finds RNAi candidates based on Elbashir's (Elbashir, 2002) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously. RNAi candidate molecules that are generated can be, for example, screened in an animal model of osmotic resistance in vivo using similar techniques as described above.

2. Expression Cassettes

OSR-1 specific RNAi of the present invention may be synthesized chemically. Chemical synthesis can be achieved by any method known or discovered in the art. Alternatively, OSR-1 specific RNAi of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex RNAi, where the two strands are synthesized separately and annealed, can also be synthesized chemically by any method known or discovered in the art. Alternatively, dsRNAs are synthesized by methods which comprise synthesis by transcription. In some embodiments, the two strands of the double-stranded region of an RNAi is expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a RNAi specific for OSR-1. In some embodiments, the transcribed dsRNA forms a single strand of a separate-stranded duplex (or double-stranded, or ds) RNA of about 18 to 25 base pairs long; thus, formation of dsRNA requires transcription of each of the two different strands of a dsRNA. The term "gene" in the expression cassette refers to a nucleic acid sequence that comprises coding sequences necessary for the production of a dsRNA. Thus, a gene includes but is not limited to coding sequences for a strand of a dsRNA.

Generally, a DNA expression cassette comprises a chemically synthesized or recombinant DNA molecule containing at least one gene, or desired coding sequence for a single strand of a dsRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

3. Vectors

In other aspects of the present invention, the compositions comprise a vector comprising a gene encoding an RNAi specific for OSR-1 or preferably at least one expression cassette comprising a promoter and a gene which encodes a sequence necessary for the production of a RNAi specific for OSR-1 (an RNAi gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone an RNAi gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of an RNAi coding sequence. The cloned plasmid DNA, linearized with a restriction enzyme, can then be used as a transcription template (See for example Milligan and Uhlenbeck. Methods in Enzymology 180: 51–64 (1989)).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising an RNAi gene (specific for OSR-1) is operatively linked to an appropriate expression control sequence(s) (promoter) to direct mRNA synthesis. In some embodiments, the gene sequence is a marker gene or a selection gene. In other embodiments of the present invention, recombinant expression vectors include origins of replication and selectable markers permitting transformation of the host cell (e.g., dihydrofolate reductase or neomycin resistance for eukaryotic cell culture). In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Preferably the design of a vector is configured to deliver the RNAi for more permanent inhibition.

4. Transfecting Cells

In yet other aspects, the present invention provides compositions comprising cells transfected by an expression cassette of the present invention as described above, or by a vector of the present invention, where the vector comprises an expression cassette (or simply the RNAi gene) of the present invention, as described above. In some embodiments of the present invention, the host cell is a nematode cell. A transfected cell may be a cultured cell or a tissue, organ, or organismal cell.

The cells may be transfected transiently or stably (e.g. DNA expressing the dsRNA is stably integrated and expressed by the host cell's genome). The cells may also be transfected with an expression cassette of the present invention, or they are transfected with an expression vector of the present invention. In some embodiments, transfected cells are are tissue, organ, or organismal cells.

In the present invention, cells to be transfected in vitro are typically cultured prior to transfection according to methods that are well known in the art, as for example by the preferred methods as defined by the American Tissue Culture Collection. In certain embodiments of the present invention, cells are transfected with dsRNAs that are synthesized exogenously (or in vitro, as by chemical methods or in vitro transcription methods), or they are transfected with expression cassettes or vectors, which express dsRNAs within the transfected cell.

In some embodiments, cells are transfected with dsDNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, consumption and pressure treatment. In alternative, embodiments, the RNAi are introduced in vivo by lipofection.

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter. In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931). It is also possible to introduce a sequence encoding a dsRNA in vivo as a naked DNA, either as an expression cassette or as a vector.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

5. Kits

The present invention also provides kits comprising at least one expression cassette comprising a RNAi gene specific for OSR-1. In some aspects, a transcript from the expression cassette forms a double stranded RNAi of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a RNAi gene, such that at least one gene encodes one strand of a RNAi that combines with a strand encoded by a second cassette to form a dsRNA; the dsRNA so produced is any of the embodiments described above. These cassettes may comprise a promoter and a sequence encoding one strand of a dsRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a dsRNA and a processing site between the sequences encoding each strand such that, when the gene is transcribed, the transcript is processed, such as by cleavage, to result in two separate strands which can combine to form a dsRNA, as described above.

In some embodiments, the present invention provides kits comprising; a) a composition comprising small interfering RNA duplexes (RNAi) configured to inhibit expression of OSR-1 protein, and b) printed material with instructions for employing the composition for treating a target cell expressing OSR-1 protein via expression of OSR-1 mRNA under conditions such that the OSR-1 mRNA is cleaved or otherwise disabled.

6. Generating OSR-1 Specific siRNA

The present invention also provides methods of synthesizing dsRNAs specific for OSR-1. The dsRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The dsRNAs synthesized in vitro, either chemically or by transcription, are used to transfect cells. Therefore, the present invention also provides methods of transfecting host cells with dsRNAs synthesized in vitro; in particular embodiments, the dsRNA are synthesized by in vitro transcription. The present invention further provides methods of silencing the OSR-1 gene in vivo by transfecting cells with dsRNAs synthesized in vitro. In other methods, the dsRNA is expressed in vitro in a transcription/translation system from an expression cassette or expression vector, along with an expression vector encoding and expressing a reporter gene.

The present invention also provides methods of expressing dsRNA in vivo by transfecting cells with expression cassettes or vectors which direct synthesis of dsRNA in vivo. The present invention also provides methods of silencing genes in vivo by transfecting cells with expression cassettes or vectors that direct synthesis of dsRNA in vivo.

VI. Agonist and Antagonist Screening Using OSR-1

As described herein, it is contemplated that OSR-1 acts in a two-component signal transduction system. Accordingly, in some embodiments, the isolated nucleic acid sequences of OSR-1 (e.g., SEQ ID NOS: 1) are used in agonist and antagonist screening applications for compounds that alter (e.g., enhance) signaling within the pathway.

A. Identification of Binding Partners

In some embodiments, binding partners of OSR-1 amino acids are identified. In some embodiments, the OSR-1 nucleic acid sequence (e.g., SEQ ID NOS: 1) or fragments thereof are used in yeast two-hybrid screening assays. For example, in some embodiments, the nucleic acid sequences are subcloned into pGPT9 (Clontech, La Jolla, Calif.) to be used as a bait in a yeast-2-hybrid screen for protein-protein interaction of a nematode cDNA library (Fields and Song *Nature* 340:245–246, (1989); herein incorporated by reference). In other embodiments, phage display is used to identify binding partners (Parmley and Smith *Gene* 73: 305–318, (1988), herein incorporated by reference).

B. Agonist and Antagonist Screening

The present invention provides methods and compositions for using OSR-1 as a target for screening compounds that can alter, for example, interaction between OSR-1 and OSR-1 binding partners (e.g., those identified using the above methods)

In one screening method, the two-hybrid system is used to screen for compounds (e.g., compound) capable of altering (e.g., inhibiting) OSR-1 function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a OSR-1 fragment and a GAL4 transactivation domain II linked to a binding partner fragment. Expression of the reporter gene is monitored and a decrease in the expression is an indication that the candidate compound inhibits the interaction of OSR-1 with the binding partner. Alternately, the effect of candidate compounds on the interaction of OSR-1 with other proteins (e.g., proteins known to interact directly or indirectly with the binding partner) can be tested in a similar manner.

In another screening method, candidate compounds are evaluated for their ability to alter OSR-1 signaling by contacting OSR-1, binding partners, binding partner-associated proteins, or fragments thereof, with the candidate compound and determining binding of the candidate compound to the peptide. The protein or protein fragments is/are immobilized using methods known in the art such as binding a GST-OSR-1 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 (1988)). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate OSR-1 physiological effects (e.g., water stress tolerance).

In another screening method, one of the components of the OSR-1/binding partner signaling system, is immobilized. Polypeptides can be immobilized using methods known in the art, such as adsorption onto a plastic microtiter plate or specific binding of a GST-fusion protein to a polymeric bead containing glutathione. For example, GST-OSR-1 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of OSR-1 with the other peptide. A variation of this method allows for the screening of compounds that are capable of disrupting a previously-formed protein/protein complex. For example, in some embodiments a complex comprising OSR-1 or a OSR-1 fragment bound to another peptide is immobilized as described above and contacted with a candidate compound. The dissolution of the complex by the candidate compound correlates with the ability of the compound to disrupt or inhibit the interaction between OSR-1 and the other peptide.

Another technique for drug screening provides high throughput screening for compounds having suitable binding affinity to OSR-1 peptides and is described in detail in WO 84/03564, incorporated herein by reference. Briefly, large numbers of different small peptide test compounds are synthesized on a solid substrate, such as plastic pins or some other surface. The peptide test compounds are then reacted with OSR-1 peptides and washed. Bound OSR-1 peptides are then detected by methods well known in the art.

Another technique uses OSR-1 antibodies, generated as discussed above. Such antibodies capable of specifically binding to OSR-1 peptides compete with a test compound for binding to OSR-1. In this manner, the antibodies can be used to detect the presence of any peptide that shares one or more antigenic determinants of the OSR-1 peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with OSR-1 and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding OSR-1 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 (1998), and Gonzales et al., Drug. Discov. Today 4:431–39 (1999)). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 (1996)), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by OSR-1 in operable association with a reporter gene (See Example 4 and Inohara et al., J. Biol. Chem. 275:27823 (2000) for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to OSR-1 of the present invention, have an inhibitory (or stimulatory) effect on, for example, OSR-1 expression or OSR-1 activity, or have a stimulatory or inhibitory effect on, for example, the expression or activity of a OSR-1 substrate. Compounds thus identified can be used to modulate the activity of target gene products (e.g., OSR-1 genes) either directly or indirectly in a therapeutic protocol, to elaborate the biological function of the target gene product, or to identify compounds that disrupt normal target gene interactions. Compounds that stimulate the activity of a variant OSR-1 or mimic the activity of a non-functional variant are particularly useful in the suppression or enhancement of water stress tolerance.

In one embodiment, the invention provides assays for screening candidate or test compounds that are substrates of an OSR-1 protein or polypeptide or a biologically active portion thereof. In another embodiment, the invention provides assays for screening candidate or test compounds that bind to or modulate the activity of a OSR-1 protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678–85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam, Anticancer Drug Des. 12:145 (1997)).

Examples of methods for the synthesis of molecular libraries can be found in the art, for example in: DeWitt et al., Proc. Natl. Acad. Sci. U.S.A. 90:6909 (1993), Erb et al., Proc. Nad. Acad. Sci. USA 91:11422 (1994), Zuckermann et al., J. Med. Chem. 37:2678 (1994), Cho et al., Science 261:1303 (1993), Carrell et al., Angew. Chem. Int. Ed. Engl. 33.2059 (1994), Carell et al., Angew. Chem. Int. Ed. Engl. 33:2061 (1994), and Gallop et al., J. Med. Chem. 37:1233 (1994).

Libraries of compounds may be presented in solution (e.g., Houghten, Biotechniques 13:412–421 (1992)), or on beads (Lam, Nature 354:82–84 (1991)), chips (Fodor, Nature 364:555–556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386–390 (1990). Devlin Science 249:404–406 (1990), Cwirla et al., Proc. Natl. Acad. Sci. 87:6378–6382 (1990), Felici, J. Mol. Biol. 222:301 (1991)).

In one embodiment, an assay is a cell-based assay in which a cell that expresses a OSR-1 protein or biologically active portion thereof is contacted with a test compound, and the ability of the test compound to the modulate OSR-1's activity is determined. Determining the ability of the test compound to modulate OSR-1 activity can be accomplished by monitoring, for example, changes in enzymatic activity. The cell, for example, can be of mammalian origin.

The ability of the test compound to modulate OSR-1 binding to a compound, e.g., a OSR-1 substrate, can also be evaluated. This can be accomplished, for example, by coupling the compound, e.g., the substrate, with a radioisotope or enzymatic label such that binding of the compound, e.g., the substrate, to a OSR-1 can be determined by detecting the labeled compound, e.g., substrate, in a complex.

Alternatively, the OSR-1 is coupled with a radioisotope or enzymatic label to monitor the ability of a test compound to modulate OSR-1 binding to a OSR-1 substrate in a complex. For example, compounds (e.g., substrates) can be labeled with $^{125}$I, $^{35}$S $^{14}$C or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., OSR-1 substrate) to interact with a OSR-1 with or without the labeling of any of the interactants can be evaluated. For example, a microphysiometer can be used to detect the interaction of a compound with a OSR-1 without the labeling of either the compound or the OSR-1 (McConnell et al. Science 257: 1906–1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and OSR-1.

In yet another embodiment, a cell-free assay is provided in which a OSR-1 protein or biologically active portion thereof is contacted with a test compound and the ability of the test compound to bind to the OSR-1 protein or biologically active portion thereof is evaluated. Preferred biologically active portions of the OSR-1 proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. A FRET binding event can be conveniently measured through standard fluorometric detection means well known in the art (e.g., using a fluorimeter).

In another embodiment, determining the ability of the OSR-1 protein to bind to a target molecule can be accomplished using real-time Biomolecular Interaction Analysis (BIA) (see, e.g., Sjolander and Urbaniczky, Anal. Chem. 63:2338–2345 (1991) and Szabo et al. Curr. Opin. Struct. Biol. 5:699–705 (1995)). "Surface plasmon resonance" or "BIA" detects biospecific interactions in real time, without labeling any of the interactants (e.g., BlAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize OSR-1, an anti-OSR-1 antibody or its target molecule to facilitate separation of complexed from non-complexed forms of one or both of the proteins, as well as to accommodate automation of the assay. Binding of a test compound to an OSR-1 protein, or interaction of an OSR-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-OSR-1 fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or OSR-1 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of OSR-1 binding or activity determined using standard techniques. Other techniques for immobilizing either OSR-1 protein or a target molecule on matrices include using conjugation of biotin and streptavidin. Biotinylated OSR-1 protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with OSR-1 protein or target molecules but which do not interfere with binding of the OSR-1 protein to its target molecule. Such antibodies can be derivatized to the wells of the plate, and unbound target or OSR-1 protein trapped in the wells by antibody conjugation. Methods for detecting such complexes, in addition to those described above for the GST-immobilized complexes, include immunodetection of complexes using antibodies reactive with the OSR-1 protein or target molecule, as well as enzyme-linked assays which rely on detecting an enzymatic activity associated with the OSR-1 protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284–7 (1993)); chromatography (gel filtration chromatography, ion-exchange chromatography); electrophoresis (see, e.g., Ausubel et al., eds. Current Protocols in Molecular Biology (1999), J. Wiley: New York.); and immunoprecipitation (see, for example, Ausubel et al., eds. Current Protocols in Molecular Biology (1999), J. Wiley: New York). Such resins and chromatographic techniques are known to one skilled in the art (See e.g., Heegaard J. Mol. Recognit 11: 141–8 (1998), Hage and Tweed J. Chromatogr. Biomed. Sci. Appl 699:499–525 (1997)). Further, fluorescence energy transfer may also be conveniently utilized, as described herein, to detect binding without further purification of the complex from solution.

The assay can include contacting the OSR-1 protein or biologically active portion thereof with a known compound that binds the OSR-1 to form an assay mixture, contacting the assay mixture with a test compound, and determining the ability of the test compound to interact with a OSR-1 protein, wherein determining the ability of the test compound to interact with a OSR-1 protein includes determining the ability of the test compound to preferentially bind to OSR-1 or biologically active portion thereof, or to modulate the activity of a target molecule, as compared to the known compound.

To the extent that OSR-1 can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, OSR-1 protein can be used as a "bait protein" in a two-hybrid assay or three-hybrid assay (see, e.g., U.S. Pat. No. 5,283,317, Zervos et al., Cell 72:223–232 (1993), Madura et al., J. Biol. Chem. 268.12046–12054 (1993), Bartel et al., Biotechniques 14:920–924 (1993), Iwabuchi et al., Oncogene 8:1693–1696 (1993), and Brent WO 94/10300; each of which is herein incorporated by reference), to identify other proteins, that bind to or interact with OSR-1 ("OSR-1-binding proteins" or "OSR-1-bp") and are involved in OSR-1 activity. Such OSR-1-bps can be activators or inhibitors of signals by the OSR-1 proteins or targets as, for example, downstream elements of a OSR-1-mediated signaling pathway.

Modulators of OSR-1 expression can also be identified. For example, a cell or cell free mixture is contacted with a candidate compound and the expression of OSR-1 mRNA or protein evaluated relative to the level of expression of OSR-1 mRNA or protein in the absence of the candidate compound. When expression of OSR-1 mRNA or protein is greater in the presence of the candidate compound than in its absence, the candidate compound is identified as a stimulator of OSR-1 mRNA or protein expression. Alternatively, when expression of OSR-1 mRNA or protein is less (i.e., statistically significantly less) in the presence of the candidate compound than in its absence, the candidate compound is identified as an inhibitor of OSR-1 mRNA or protein expression. The level of OSR-1 mRNA or protein expression can be determined by methods described herein for detecting OSR-1 mRNA or protein.

A modulating agent can be identified using a cell-based or a cell free assay, and the ability of the agent to modulate the activity of an OSR-1 protein can be confirmed in vivo, e.g., in a nematode.

Experimental

The following examples are provided in order to demonstrate and further illustrate certain preferred embodiments and aspects of the present invention and are not to be construed as limiting the scope thereof.

A. Methods

Strains and Culture Conditions

*C. elegans* worms were cultured at 22° C. under standard growth conditions (Brenner, Genetics 77: 71–94 (1974). Strains used in this study were: Bristol strain N2 (wild-type), osr-1(rm1), unc-73(e936);dpy-5(e61), age-1(hx546), daf-16 (mgdf50), osm-9(ky10), ocr-2(ak47), osm-10(n1052), unc- 43(n1186), sek-1(km4), nsy-1(ky397), pmk-3(ok169), jnk-1(jk7),jkk-1(km2), and mek-1(ks54).

Genetic Screens for Osmotic Stress Resistance (OSR) Mutants

Standard ethyl methane sulphonate (EMS) mutagenesis (Brenner, ibid.) was performed on N2 strain hermaphrodites. The F2 generation (~20,000 haploid genomes) was screened for mutants that maintained normal swimming behavior on NGM agar plates containing 500 mM NaCl (high salt plates) for more than 15 minutes (acute motility assay). Putative mutants that showed normal motility in this assay were isolated for further analysis.

Mapping and Cloning of OSR-1

Standard mapping procedures (Brenner, ibid) were used to map OSR-1 to chromosome I. We used three-factor mapping to identify OSR-1 on −0.2 m.u between DPY-5 and UNC-73. Individual cosmids from the identified genetic interval were injected into osr-1(rm1) animals at 40 ng/μl with 100 ng/μl myo-2::gfp plasmid as a co-injection marker. Rescue experiments were performed with at least 3 independent transgenic lines.

Behavioral and Stress Resistance Assays

Worms were placed on high salt plates containing 500 mM NaCl and scored for their motility over a period of 10 minutes (acute motility assay) and after 1, 5, 12 hours (chronic adaptation assay). Osmotic stress survival assays were performed on the high salt plates seeded with E. coli (OP50). To score for viability, worms were collected from the salt plates using a recovery buffer (300 mM NaCl in M9), transferred to regular NGM plates (50 mM NaCl), and allowed to recover overnight before scoring for viability. Osmotic avoidance behavior (OSM) was quantified as the percentage of worms that crossed a 2 cm ring of 4 M NaCl or 8 M Fructose, on NGM agar plate, within 5 minutes. Nose touch response, 1-octanol repellent assays (Hart, J Neurosci 19: 1952–1958), heat Lithgow et al., Proc Natl Acad Sci U.S.A. 92: 7540–7544 (1995), and oxidative stress (Lee et al., Nat Genetics 33:40–48) experiments were performed as described previously. Statistical significance between mutants in the behavioral and stress assays was determined using the two-tailed t-test and by a one-way ANOVA test.

Molecular Biology

The functional OSR-1::GFP operon construct and the tissue specific expression constructs were generated using the Gateway system (Invitrogen) (Walhout et al., Methdos Enzymol 328: 575–592 (2000). The rescuing fragment (pASRM1) or the heterologous promoter::OSR-1 cDNA was inserted into a pEntry vector containing the SL2-GFP operon cassette. The promoters used were dpy-7 (hypodermal), vha-6 (intestine) (Wang et al., Development 129: 4989–4998), and F25B3.3 (pan-neuronal) (Altun-Gultekin et al., Development 128: 1951–1969 (2001). The full transcription unit of OSR-1 was determined using a partial EST (yk563c9) obtained from Yuji Kohara and using a SMART RACE cDNA kit (Clontech).

RNA Interference (RNAi) Experiments

RNAi experiments were performed using a feeding method (Timmons et al., Gene 263: 103–112 (2001). For OSR-1 RNAi, pAS1 was constructed by sub-cloning the OSR-1 cDNA (1932 bp) into the L4440 vector. For PMK-1/p38 RNAi, the pDK177 plasmid was used (Kim et al., Science 297: 942–946 (2002). Eggs were hatched on E. coli (HT115) carrying the L4440 expression vector (control groups), HT115 carrying pDK177 plasmid (PMK-1), or the plasmid pAS1 (OSR-1), and allowed to grow for three days (adult stage). For knockdown of both PMK-1 and OSR-1, eggs were hatched on plates containing equal amounts of bacteria expressing dsRNA for both PMK-1 and OSR-1. Animals that were grown on the RNAi plates were exposed to 500 mM NaCl for 24 hours and scored for viability as mentioned above. Efficiency of the feeding RNAi was confirmed using the one-step RT-PCR kit (Invitrogen).

B. Results

When wild-type (N2 strain) animals are exposed to acute osmotic stress (10 minutes, 500 mM NaCl), a complete loss of motility and reduction in body volume of the worms was observed (FIG. 1A-1D, and FIG. 2A). Upon transfer to normal growth medium (50 mM NaCl), the animals recovered their original body size and regained normal motility within minutes (FIG. 1E-1G). However, prolonged exposure of N2 worms to high salt concentrations, severely affects motility and viability. After 5 hours of exposure to 500 mM NaCl, most N2 animals were immotile; those that were motile (43%) (FIG. 2B) exhibited sluggish swimming behavior. Prolonged exposure to high osmotic stress was eventually lethal. After 24 hours 87% of the wild-type animals were dead (FIG. 2C).

To identify genes mediating the osmotic stress responses in C. elegans, a genetic screen to isolate mutants that are osmotic stress resistant (OSR) at 500 mM NaCl was designed. Mutants that maintained normal motility on the high salt plates for 15 minutes were isolated for further analysis. Among 104 isolated mutant strains, four different complementation groups were identified: osr-1, osr-2, osr-3, and osr-4.

Figure 2:
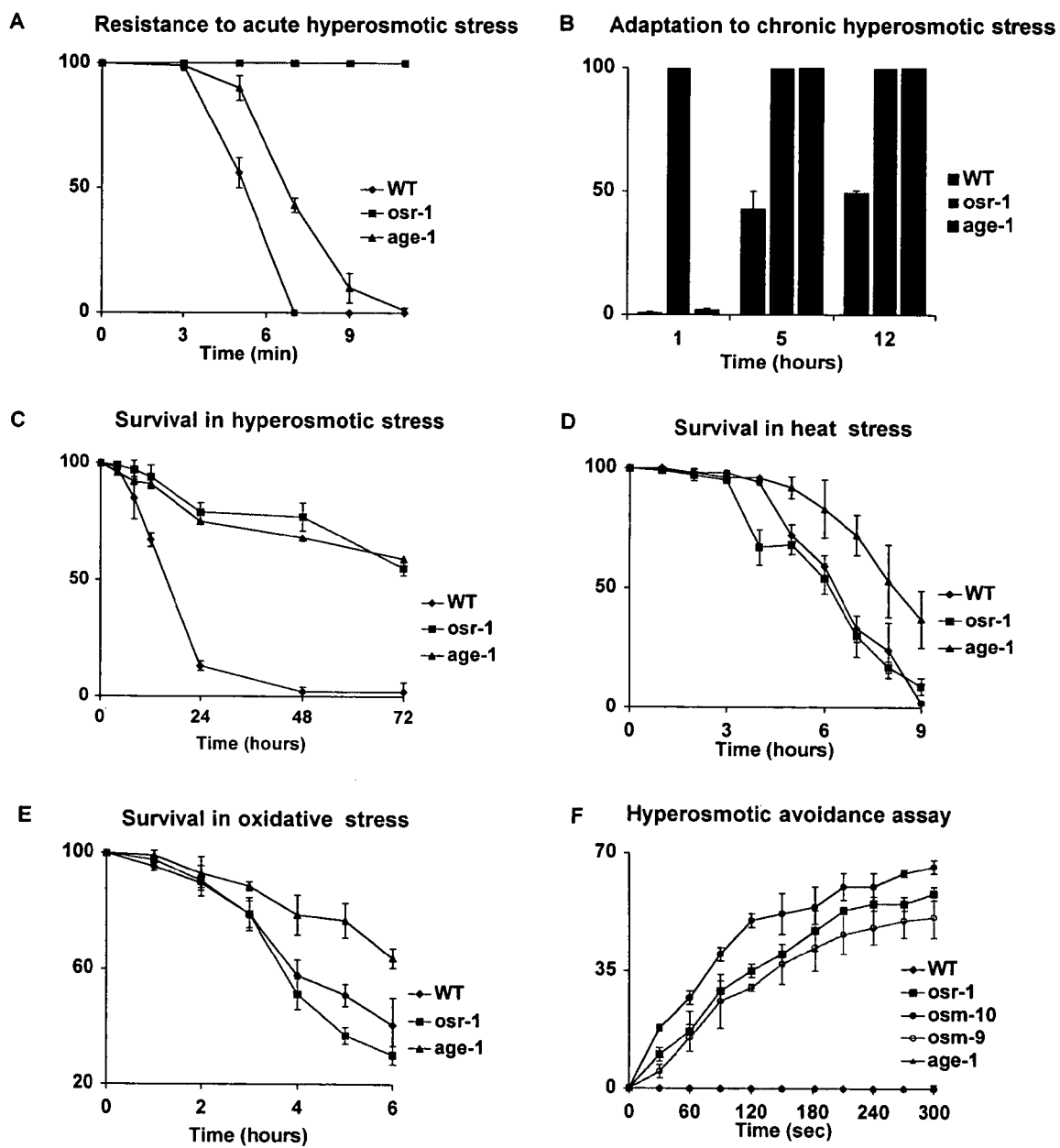
FIG. 2 shows that osr-1(rm1) worms are specifically resistant to osmotic stress.

Osr-1(rm1) Mutants are Specifically Resistant to Osmotic Stress osr-1(rm1) animals were observed to have an enhanced ability to resist hyperosmotic stress (FIGS. 1 and 2). In contrast to N2 animals, osr-1(rm1) animals exhibit normal swimming behavior (FIG. 1H-1K) when exposed to a transient osmotic stress (10 min, 500 mM NaCl), and remain viable (88%) even after 24 hours (FIG. 2C). osr-1(rm1) animals are also resistant to osmotic stress caused by sorbitol, glucose, sucrose and KCl, demonstrating that osr-1 (rm1) animals have a general resistance to hyperosmotic stress.

To determine whether the osr-1(rm1) mutation is specific to osmotic stress or confers resistance to multiple stresses, as is observed for long-lived mutants of the insulin-like signaling (ELS) pathway (Dorman et al., Genetics 41: 1399–1406 (1995), Kenyon et al., Nature 366: 461–464 (1993), Kimura et al., Science 277: 942–946 (1997), Larsen, Proc Natl Acad Sci U.S.A. 90: 8905–8909 (1993), Lithgow et al., Proc Natl Acad Sci U.S.A. 92: 7540–7544 (1995), Murakami and Johnson, Genetics 143: 1207–1218 (1996), Tissenbaum and Ruvkin, Genetics 148: 703–717 (1998)), we tested for the ability of osr-1(rm1) animals to survive heat-shock (35 C) or oxidative stress (300 mM paraquat) (FIG. 2D-2E). In contrast to age-1(hx546) animals, osr-1 (rm1) animals were sensitive to both stresses (P<0.05). Moreover, osr-1(rm1) did not exhibit other phenotypes associated with general stress resistance as seen in other ILS pathway mutants, such as extended lifespan or constitutive dauer formation. Thus, osr-1(rm1) animals are a newly discovered class of mutants that are resistant specifically to osmotic stress.

OSR-1 and AGE-1 have Critical Roles in Resistance to Chronic Osmotic Stress

We explored the possibility that age-1(hx546) animals were resistant to osmotic stress in a manner similar to osr-1(rm1) animals. As shown in FIG. 2A, exposure of the general stress resistant mutant, age-1(hx546) to 500 mM NaCl, caused a complete loss of motility and reduction in body volume within 11 minutes, similar to wild-type animals. This demonstrates that age-1(hx546) animals are not pre-adapted to acute osmotic stress like osr-1(rm1) animals (FIG. 2A). In addition, and in contrast to osr-1(rm1) animals, age-1(hx546) animals have a wild-type phenotype for osmotic avoidance (FIG. 2F). age-1(hx546) animals exhibited similar motility and viability as the osr-1(rm1) animals upon prolonged exposures to high osmotic environments (FIG. 2B-2C). These results indicate that although AGE-1 does not regulate osmotic avoidance or resistance to acute osmotic stress, both OSR-1 and AGE-1 regulate survival under conditions of prolonged hyperosmotic stress.

Figure 5:
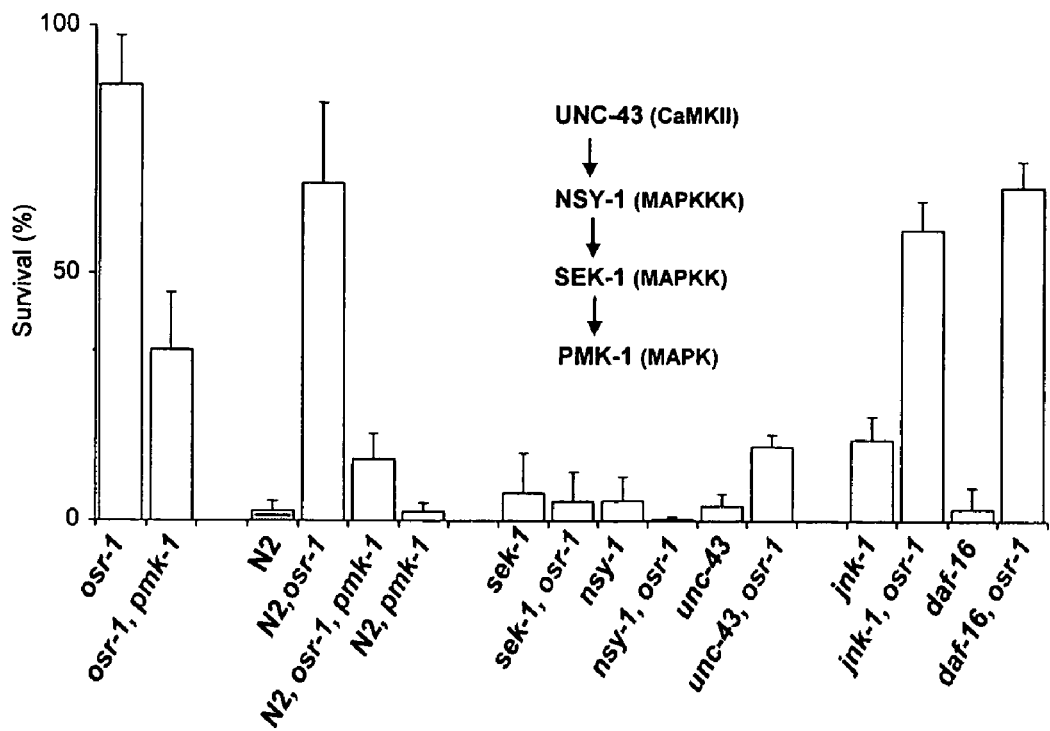
FIG. 5 shows that OSR-1 genetically interacts with the UNC-43/CaMKII and the conserved PMK-1/p38 MAPK signaling pathway to promote survival in osmotic stress.

In C. elegans, AGE-1 represses the forkhead transcription factor, DAF-16, to promote stress resistance and longevity (Henderson and Johnson, Curr Biol 11: 1975–1980 (2001), Murakami and Johnson Genetics 143: 1207–1218 (1996), Ogg et al., Nature 389: 994–999 (1997)). To test if DAF-16 is required for the ability of OSR-1 to regulate resistance to hyperosmotic environments, a null mutant of DAF-16 (Ogg et al., Nature 389: 994–999 (1997) was knocked down for OSR-1 by feeding RNAi. As shown in FIG. 5A, the ability of OSR-1 to regulate survival in hyperosmotic environments is not dependent on DAF-16.

Osr-1(rm1) Animals Display an Osmotic Avoidance Abnormality (OSM) Phenotype

The observed osmotolerance of osr-1(rm1) animals led to experiments designed to test whether OSR-1 is involved in detection of high osmolarity environments as was described previously for osmotic avoidance defective (OSM) mutants (Bargamann et al., Cold Spring Harb Sym Quant Biol 55: 529–538 (1990), Culloti and Russell Genetics 90: 243–256 (1978)). osr-1(rm1) animals exhibited an osmotic avoidance abnormality phenotype as they fail to avoid regions of 4 M NaCl or 8 M Fructose (FIG. 2F). The osmotic avoidance defect of osr-1(rm1) animals is of a magnitude similar to that seen in the previously characterized osm mutants, such as osm-9(ky10) (Colbert et al., J Neruosci 17: 8259–8269 (1997), osm-10(n1052) (Hart et al., J Neurosci 19: 1952–1958 (1999)), and ocr-2(ak47) (Tobin et al., Neuron 35: 307–318 (2002)).

Osmosensation in C. elegans is dependent on the integrity of osmosensory organs (amphids and phasmids) and function of the ASH neurons; the defective osmotic avoidance phenotype in osm-9(ky10), osm-10(n1052), and ocr-2(ak47) has been ascribed to impaired function of the ASH neurons (Colbert et al., J Neruosci 17: 8259–8269 (1997), (Hart et al., J Neurosci 19: 1952–1958 (1999), (Tobin et al., Neuron 35: 307–318 (2002). Based on lipophilic dye staining, no morphological abnormalities in the osmosensory organs (amphids and phasmids) of osr-1(rm1) animals were detected. In addition, osr-1(rm1) animals have normal responses to nose touch and the repellent 1-octanol, which are also mediated by the polymodal ASH neurons via distinct signaling pathways (Hart et al., J Neurosci 19: 1952–1958 (1999), Kaplan and Horvitz, Proc Natl Acad Sci U.S.A. 90: 2227–2231 (1993). Hence, the present results demonstrate that mechanosensory and chemosensory responses mediated by the ASH neurons are normal in osr-1(rm1 animals.

Unlike osr-1(rm1) animals, other osmotic avoidance defective mutants, osm-9(ky10), ocr-2(ak47), and osm-10 (n1052) are not resistant to either acute or chronic osmotic stress. Also, none of these mutations affect osmotic stress tolerance in OSR-1 deficient animals. This demonstrates that the osmosensory pathway defined by OSM-9, OCR-2, and OSM-10, does not mediate acute or chronic resistance to osmotic stress, and that the hyper-resistance of osr-1(rm1) animals is independent of the pathways regulated by the OSM genes tested here.

Positional Cloning, Sequence Analysis and Expression Patterns of OSR-1

OSR-1 was cloned using standard two and three-factor mapping, and transformation rescue approaches (FIG. 3A). Two cosmids, C32E12 and F56A3, with an overlapping region of 11 kb gave a full rescue of the osr-1(rm1) phenotypes. In this overlapping region, a 4 kb minimal rescuing fragment (pASRM1) was identified containing a single predicted gene C32E12.3, that completely rescued all the osr-1(rm1) phenotypes. In osr-1(rm1) worms, a G-to-A mutation at a predicted splice acceptor site in the transcription unit of C32E12.3 (FIG. 3B) was found. Introduction of this mutation in pASRM1 completely eliminated its ability to rescue the osr-1(rm1) animals phenotypes. In addition, RNAi of OSR-1 in wild-type animals results in osr-1(rm1)-like phenotypes, indicating that that the OSR-1 gene corresponds to C32E12.3.

Figure 4:
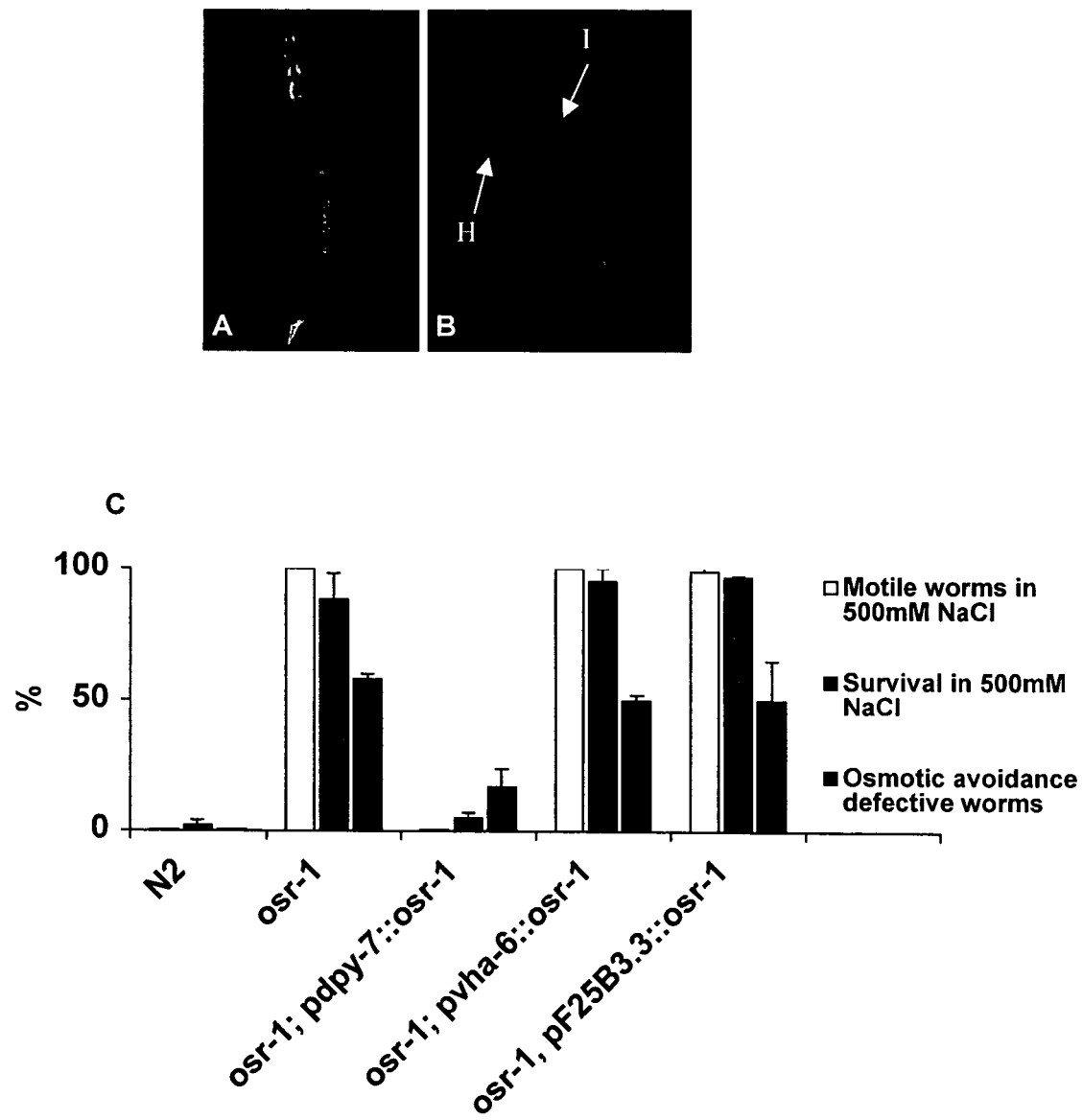
FIG. 4 shows that OSR-1 is expressed in the hypodermis and intestine.

The OSR-1 gene encodes a predicted protein of 643 amino acids (FIG. 3C), and lacks domains that would suggest a specific molecular function. To identify the tissues in which OSR-1 is expressed and functions, the rescuing fragment, pASRM1, was placed in an artificial operon with GFP. This construct fully rescued the osr-1(rm1) phenotypes, and GFP fluorescence was seen in the hypodermis and intestine during all developmental stages (FIGS. 4A–4B). To test which tissues have functional importance, rescue experiments were performed using heterologous promoter constructs including hypodermal ($P_{dpy-7}$::OSR-1::GFP), intestinal ($P_{vha-6}$::OSR-1::GFP) (Wang et al., Development 129: 4989–4998 (2002)), and pan-neuronal ($P_{F25B3.3}$::OSR-1:: GFP) promoters (Altun-Gultekin et al., Development 128: 1951–1969 (2001). Consistent with an important role for the hypodermis in osmoregulation in C. elegans (Petalcorin et al., J Mol Biol 294: 347–355 (1999)), only hypodermal expression of OSR-1 cDNA fully rescues the osr-1(rm1) phenotypes (FIG. 4C).

OSR-1 Interacts with the p38 MAPK Cascade

To further charactertize OSR-1 regulation of osmotic stress responses in C. elegans, the role of the C. elegans homologs of HOG/p38 MAP kinase signaling pathway (Brewster et al., Science 259: 1760–1763 (1993)) in mediating phenotypes seen in osr-1(rm1) animals was investigated. In C. elegans, there are multiple MAPK encoding genes implicated in development and resistance to abiotic and biotic stresses (Kurz and Ewbank, Nat Rev Genet 4: 380–390 (2003)). Two MAPK pathways in C. elegans include the Esp pathway (ESP-8/MAPKKK→ESP-2/ MAPKK→PMK-1/p38/MAPK), which functions in pathogen resistance (Kim et al., Science 297: 623–626 (2002)), and the neuronal symmetry (Nsy) pathway (UNC-43/ CaMKII→NSY-1/ESP-8→SEK-1/ESP-2→unknown MAPK), that mediates asymmetric neuronal cell fate in AWC sensory neurons (Sagasti et al., Cell 105: 221–232 (2001), Tanaka-Hino et al., EMBO Rep 3: 56–63 (2002)).

Down-regulation of PMK-1/p38 in osr-1(rm1) worms by feeding RNAi significantly reduced their ability to survive chronic osmotic stress (FIG. 5A, P<0.05). Similarly, null mutations of the upstream components of the Esp and Nsy pathways, NSY-1 and SEK-1, completely suppressed the ability of OSR-1 deficient animals to survive osmotic stress (FIG. 5A). Next, the potential relationship between OSR-1 and the most upstream component of the NSY pathway, UNC-43 was investigated. As shown in FIG. 5A, UNC-43, the only identified CaMKII in *C. elegans* (Reiner et al., Nature 402: 199–203 (1999)), is also essential for viability under chronic osmotic stress. The present invention is not limited t0 any particular mechanisms. Indeed, an understanding of the mechanism is not necessary to practice, make or use the present invention. Nevertheless, it is contemplated that these data demonstrate that OSR-1 regulates osmotic stress survival through a newly discovered arrangement of a MAPK cascade that includes components of both the Esp and Nsy pathways (see FIG. 5B).

The interactions between OSR-1 and the CaMKII mediated p38 pathway are specific. For example, mutations in genes that mediate heavy metal resistance including JNK-1, JKK-1 (Villanueva et al., Methods Enzymol 328: 575–592 (2000)), and MEK-1 (Koga et al., Embo J 19: 5148–5156 (2000)) do not suppress OSR-1 phenotypes (FIG. 5A). The present invention is not limited to any particular mechanisms. Indeed, an understanding of the mechanism is not necessary to practice, make or use the present invention. Nevertheless, it is contemplated that these results indicate that OSR-1 functions upstream of, or in parallel to, UNC-43/CaMKII and a conserved p38 signaling pathway in promoting survival under chronic osmotic stress (FIG. 5B).

The role of PMK-1/p38 MAPK pathway in regulating resistance to acute dehydration and osmotic avoidance defects seen in osr-1(rm1) animals was also investigated. osr-1(rm1), pmk-1(RNAi) animals remained resistant to the acute effects of osmotic stress by maintaining normal swimming behavior (100% motile animals after 10 minutes, N=175). In addition, the animals retain the OSM-like phenotype, as 57% of osr-1(rm1), pmk-1(RNAi) worms cross the 4 M NaCl ring, similar to the phenotypes seen in osm-9(ky10) and osr-1(rm1) animals (P>0.05) (FIG. 2F).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A composition comprising an isolated collection of mutant *C. elegans* altered in an (OSR-1 gene to reduce sensitivity to osmotic desiccation stress compared to *C. elegans* not altered in said OSR-1 gene, wherein said mutant *C. elegans* comprise a knock-out OSR-1 mutation.

2. The composition of claim 1, wherein said mutant *C. elegans* comprise a knock-out (OSR-1 mutation generated via ethyl methane sulphonate mutagenesis.

3. The composition of claim 1, wherein said collection of mutant *C. elegans* is configured for administration to a host.

4. The composition of claim 3, wherein said host comprises a plant.

5. The composition of claim 3, wherein said host comprises an animal.

6. A composition comprising
   a small interfering RNA duplex, or vectors encoding said small interfering RNA duplex, configured to inhibit expression of *C. elegans* OSR-1 protein, and a nucleic acid transfecting agent.

* * * * *

```
                              SEQUENCE LISTING

<160> NUMBER OF SEQ ID NOS: 6

<210> SEQ ID NO 1
<211> LENGTH: 1932
<212> TYPE: DNA
<213> ORGANISM: Caenorhabditis elegans

<400> SEQUENCE: 1
atgattttat ttttattttt attcctgttg ttaggatttt gtatcgcacc attatcggcc      60
caatctccat cgacttccga tgctccggga gctttgttgt catctctcgt aggtaaaagc     120
catcaaaaac taccactggc tccatcaatg gaagctcttg aactgatggg tgttcaattt     180
gttgatgctc tcatcaaaaa aggtcaaatg gaaatggcaa aaggagcatt taagactcaa     240
ttagaagttc tagagaaagt acatcctgat caattcgata agtacaaaaa gctaaaagtt     300
gatgatttgg cagctgatgc agttatgcaa caggcggaga tggcaaaatt acagcctaaa     360
tcaggaaatg catttatcga tatgttgaat ggaaatggaa tcccaattgg tagcagtatt     420
cgtggattag aagatgctat ccgaacgcag agagatatgg aaaatacgga tccgtccgaa     480
cagattgcca aagccgtaat ggacaaattt caaacacaaa ttctcccagg actcgttgca     540
aatatgatcg ctggcaagaa cccctttaaa atgcctcaac aaatgagaaa agctcaagct     600
gctccatcgt cagtgttcca acaagctctt gctcaaagag caatgttagg taaaaatgcc     660
ccagttgccg gtggaagagg tgaagaacaa cggatgatga tgaatcgagt ggaccaaaga     720
atgcaacaaa gagaacttca agaggaagat gaagatgatg atgatcttga ggacgaggat     780
gtacccagaa gaagaagttc ggatggagaa ccacaaagtg aagcagagca tcagagaaga     840
gatttagcca ggagattgaa aagtagtcct agattaaaag agcttttaca gaatgcggaa     900
gttcaatcat tgctctctta ccaacgaatg agggattctc cactgagcaa gcgaaggcct     960
```

-continued

```
ttggctatga acgatgagga tgaaagtgca ttccgcgcaa tggaggctcg tgcaaaacta    1020
gatcaaaaat ctcaacttgt gctcggtctc catggttttg gagagtctga tgatgatgaa    1080
gacgaagaag atgaaaattt gattgatcca tctgaaaatt cattccgtcg tgcaccactt    1140
cgtctttctt ccggattcgt tgagaaatta agtcaaatg atgaattgaa aagtgcattg     1200
gacagaatta aatatcgagt tgatgacgtg gaaaagtatc ttgctccaaa gccgatggaa    1260
ttcaatccaa aacctcagcc tggctacttt gctccacgta aaatcccaac aagaccacgt    1320
aaaatgcttc cattattaat tggatctgat ccaaaagttc aagaggaaat acgaagacat    1380
ccaagtaccg aatggaaaat tgcaaaagaa tcagagtttt tgacaaattt gaagaataat    1440
ccaagtcttg ctgcattgtt catggatgat aaattagaga atacattgaa aggaaggcaa    1500
atgttaactg atgaacagaa aggtagaaca cgtgtcaaaa caattcgtgc attaccaaga    1560
ctgttcggtg caccaactgc aaaagctgaa atgattgatg caaaggtatt ccaagatatt    1620
gaagaacgtc ccattcctcc attgttcttt gaaccaaaag gaaggcatac gagattgaga    1680
tggactggag caaatgaaaa agaaattcca ggacttggaa gtcgcttcat tctcccatct    1740
cttgatccaa ctatgccagc cttgaacacg gctttctcga ctcaggggcg agcccgtgac    1800
gagtgggata ccatgttcaa atcccgaat aactggaatc ctggagatga agttgggttc     1860
aaaatgaact caaaaaccaa acgattcgtt ggaggaaatg gagcatttga tatgcctgca    1920
ctgggattgt ag                                                        1932
```

<210> SEQ ID NO 2
<211> LENGTH: 643
<212> TYPE: PRT
<213> ORGANISM: Caenorhabditis elegans

<400> SEQUENCE: 2

```
Met Ile Leu Phe Leu Phe Leu Phe Leu Leu Gly Phe Cys Ile Ala
1               5                   10                  15

Pro Leu Ser Ala Gln Ser Pro Ser Thr Ser Asp Ala Pro Gly Ala Leu
            20                  25                  30

Leu Ser Ser Leu Val Gly Lys Ser His Gln Lys Leu Pro Leu Ala Pro
        35                  40                  45

Ser Met Glu Ala Leu Glu Leu Met Gly Val Gln Phe Val Asp Ala Leu
    50                  55                  60

Ile Lys Lys Gly Gln Met Glu Met Ala Lys Gly Ala Phe Lys Thr Gln
65                  70                  75                  80

Leu Glu Val Leu Glu Lys Val His Pro Asp Gln Phe Asp Lys Tyr Lys
                85                  90                  95

Lys Leu Lys Val Asp Asp Leu Ala Ala Asp Ala Val Met Gln Gln Ala
            100                 105                 110

Glu Met Ala Lys Leu Gln Pro Lys Ser Gly Asn Ala Phe Ile Asp Met
        115                 120                 125

Leu Asn Gly Asn Gly Ile Pro Ile Gly Ser Ser Ile Arg Gly Leu Glu
    130                 135                 140

Asp Ala Ile Arg Thr Gln Arg Asp Met Glu Asn Thr Asp Pro Ser Glu
145                 150                 155                 160

Gln Ile Ala Lys Ala Val Met Asp Lys Phe Gln Thr Gln Ile Leu Pro
                165                 170                 175

Gly Leu Val Ala Asn Met Ile Ala Gly Lys Asn Pro Phe Lys Met Pro
            180                 185                 190

Gln Gln Met Arg Lys Ala Gln Ala Ala Pro Ser Ser Val Phe Gln Gln
```

```
            195                 200                 205
Ala Leu Ala Gln Arg Ala Met Leu Gly Lys Asn Ala Pro Val Ala Gly
            210                 215                 220

Gly Arg Gly Glu Glu Gln Arg Met Met Met Asn Arg Val Asp Gln Arg
225                 230                 235                 240

Met Gln Gln Arg Glu Leu Gln Glu Glu Asp Glu Asp Asp Asp Asp Leu
                245                 250                 255

Glu Asp Glu Asp Val Pro Arg Arg Ser Ser Asp Gly Glu Pro Gln
            260                 265                 270

Ser Glu Ala Glu His Gln Arg Arg Asp Leu Ala Arg Arg Leu Lys Ser
            275                 280                 285

Ser Pro Arg Leu Lys Glu Leu Leu Gln Asn Ala Glu Val Gln Ser Leu
290                 295                 300

Leu Ser Tyr Gln Arg Met Arg Asp Ser Pro Leu Ser Lys Arg Arg Pro
305                 310                 315                 320

Leu Ala Met Asn Asp Glu Asp Glu Ser Ala Phe Arg Ala Met Glu Ala
                325                 330                 335

Arg Ala Lys Leu Asp Gln Lys Ser Gln Leu Val Leu Gly Leu His Gly
            340                 345                 350

Phe Gly Glu Ser Asp Asp Glu Asp Glu Glu Asp Glu Asn Leu Ile
                355                 360                 365

Asp Pro Ser Glu Asn Ser Phe Arg Arg Ala Pro Leu Arg Leu Ser Ser
            370                 375                 380

Gly Phe Val Glu Lys Leu Lys Ser Asn Asp Glu Leu Lys Ser Ala Leu
385                 390                 395                 400

Asp Arg Ile Lys Tyr Arg Val Asp Asp Val Glu Lys Tyr Leu Ala Pro
                405                 410                 415

Lys Pro Met Glu Phe Asn Pro Lys Pro Gln Pro Gly Tyr Phe Ala Pro
            420                 425                 430

Arg Lys Ile Pro Thr Arg Pro Arg Lys Met Leu Pro Leu Leu Ile Gly
            435                 440                 445

Ser Asp Pro Lys Val Gln Glu Glu Ile Arg Arg His Pro Ser Thr Glu
450                 455                 460

Trp Lys Ile Ala Lys Glu Ser Arg Val Leu Thr Asn Leu Lys Asn Asn
465                 470                 475                 480

Pro Ser Leu Ala Ala Leu Phe Met Asp Asp Lys Leu Glu Asn Thr Leu
                485                 490                 495

Lys Gly Arg Gln Met Leu Thr Asp Glu Gln Lys Gly Arg Thr Arg Val
            500                 505                 510

Lys Thr Ile Arg Ala Leu Pro Arg Leu Phe Gly Ala Pro Thr Ala Lys
            515                 520                 525

Ala Glu Met Ile Asp Ala Lys Val Phe Gln Asp Ile Glu Glu Arg Pro
            530                 535                 540

Ile Pro Pro Leu Phe Phe Glu Pro Lys Gly Arg His Thr Arg Leu Arg
545                 550                 555                 560

Trp Thr Gly Ala Asn Glu Lys Glu Ile Pro Gly Leu Gly Ser Arg Phe
                565                 570                 575

Ile Leu Pro Ser Leu Asp Pro Thr Met Pro Ala Leu Asn Thr Ala Phe
            580                 585                 590

Ser Thr Gln Gly Arg Ala Arg Asp Glu Trp Asp Thr Met Phe Lys Ile
            595                 600                 605

Pro Asn Asn Trp Asn Pro Gly Asp Glu Val Gly Phe Lys Met Asn Ser
            610                 615                 620
```

Lys Thr Lys Arg Phe Val Gly Gly Asn Gly Ala Phe Asp Met Pro Ala
625                 630                 635                 640

Leu Gly Leu

<210> SEQ ID NO 3
<211> LENGTH: 2993
<212> TYPE: DNA
<213> ORGANISM: Caenorhabditis elegans

<400> SEQUENCE: 3

| | | | | | |
|---|---|---|---|---|---|
| ctcaaagcca | atcaactcta | ctcacttttc | ttcagaacct | taacttttg | tgtcactttc | 60 |
| cccaaaaacc | gttcaagctg | ctgccttcac | tctcatcccc | tcctcttact | ccttctttct | 120 |
| cgtccgctac | tactgtatct | tctggacatc | tacctgtata | cacaccagtg | gccagtcatc | 180 |
| tgccattaca | atttcatcaa | ttgacacttc | ttcaacaaca | accgccgtcc | tcattcactc | 240 |
| ccgattcttc | ctcatcctca | acatcgtcgt | ctttggctga | aattcccgaa | gacgttatga | 300 |
| tggagatgct | ggtagatcag | ggaactgatg | catcgtcatc | cgcctccacg | tccacctcat | 360 |
| ctgtttcgag | attcggagcg | gacacgttca | tgaatacacc | ggatgatgtg | atgatgaatg | 420 |
| atgatatgga | accgattcct | cgtgatcggt | gcaatacgtg | gccaatgcgt | aggccgcaac | 480 |
| tcgaaccacc | actcaactcg | agtcccatta | ttcatgaaca | aattcctgaa | gaagatgctg | 540 |
| acctatacgg | gagcaatgag | caatgtggac | agctcggcgg | agcatcttca | aacgggtcga | 600 |
| cagcaatgct | tcatactcca | gatggaagca | attctcatca | gacatcgttt | ccttcggaaa | 660 |
| tgtccgaatc | gccagacgat | accgtatcgg | gaaaaaagac | aacgaccaga | cggaacgctt | 720 |
| ggggaaatat | gtcatatgct | gaacttatca | ctacagccat | tatggctagt | ccagagaaac | 780 |
| ggttaactct | tgcacaagtt | tacgaatgga | tggtccagaa | tgttccatac | ttcagggata | 840 |
| agggagattc | gaacagttca | gctggatgga | agaactcgat | ccgtcacaat | ctgtctcttc | 900 |
| attctcgttt | catgcgaatt | cagaatgaag | gagccggaaa | gagctcgtgg | tgggttatta | 960 |
| atccagatgc | aaagccagga | aggaatccac | ggcgtacacg | tgaacgatcc | aatactattg | 1020 |
| agacgactac | aaaggctcaa | ctcgaaaaat | ctcgccgcgg | agccaagaag | aggataaagg | 1080 |
| agagagcatt | gatgggctcc | cttcactcga | cacttaatgg | aaattcgatt | gccggatcga | 1140 |
| ttcaaacgat | ttctcacgat | ttgtatgatg | atgattcaat | gcaaggagca | tttgataacg | 1200 |
| ttccatcatc | tttccgtccc | cgaactcaat | cgaacctctc | gattcctgga | tcgtcgtctc | 1260 |
| gtgtttctcc | agctattgga | agtgatatct | atgatgatct | agaattccca | tcatgggttg | 1320 |
| gcgaatcggt | tccagcaatt | ccaagtgata | ttgttgatag | aactgatcaa | atgcgtatcg | 1380 |
| atgcaactac | tcatattggt | ggagttcaga | ttaagcagga | gtcgaagccg | attaagacgg | 1440 |
| aaccaattgc | tccaccacca | tcataccacg | agttgaacag | tgtccgtgga | tcgtgtgctc | 1500 |
| agaatccact | tcttcgaaat | ccaattgtgc | caagcactaa | cttcaagcca | atgccactac | 1560 |
| cgggtgccta | tggaaactat | caaaatggtg | gaataactcc | aatcaattgg | ctatcaacat | 1620 |
| ccaactcatc | tccactgcct | ggaattcaat | cgtgtgaat | tgtagctgca | cagcatactg | 1680 |
| tcgcttcttc | atcggctctt | ccaattgatt | tggaaaatct | gacacttccc | gatcagccac | 1740 |
| tgatggatac | tatggatgtt | gatgcattga | tcagacatga | gctgagtcaa | gctggagggc | 1800 |
| agcatattca | ttttgatttg | taaattctct | tcattttgtt | tcccctggtg | ttgttcgaaa | 1860 |
| gagagatagc | aaagcagcga | ggagtgagaa | atcttccgtc | ttcatctttt | caaatccctc | 1920 |
| cctacacaca | ctcaacgatc | atcacagcca | gaccatcaat | attcttccaa | attttgacgt | 1980 |

-continued

```
cgttaattttt ttttcagttt tttcaaaaac tctattttct attttctgtc gtttgttccc    2040
ctttctctcg tctaattcca acacattcat cccagtgacg tcgtgtaata ataatataaa    2100
atacctcttc tctctttctt ccctaatgc gaaatatcga aaaccgttg attattacct     2160 ctttttctt gtttttttt tctctctctc tctcccgtca tccaggttct tcactcttta     2220
aatgctacct ctatcccatc tttttcgctg taaatttgtt tcgcaatcaa actgctaaa    2280 acacattccc caatctgtct tttttaattg aattttcaa aaatttgat tcttgattt      2340 ctcttgtaat tctttaattt tcctcttttt tttccccctg gtagcaaatg tctagcgatt   2400
ctctttcttt ttttgtttaa ctttcacatc tggccgattc gaatcctccg tatacacaca   2460
cacatagtaa tctacctcca aaattttact gaaagatgtg atcccctctc tgtctccctc   2520
tacaaaacat tatttgtctg tttgtgtata ttgccaccac gtcgatttta aattaaaacc   2580
atcgtttttt cttcttttct acttttttct cgaaaaattt aacaacacac aaaaaaatcc   2640
ttcaaaaaat ctcagtttta aatggtgtgg caatatatcg atcccctc tacaccagaa     2700 cagtcttgca atttcagaga atgatttca gattttcat atcacaggcc ccctttttt     2760 gcttgttttt ttctctacct ctctttcttt tcattctatt tctctctctt gttttctctc   2820
tgttatcctg tacattttcc ttccaattct ttctggctat ttctgatttt cgagttcata   2880
ttctctacgt ctcactttct ctcgcgccac gccccctttt tcgtctccct ccgcccccaa   2940
atatatttgc gactgtatga tgatgatgat gatttaataa aaatcaaatt tga          2993
```

<210> SEQ ID NO 4
<211> LENGTH: 530
<212> TYPE: PRT
<213> ORGANISM: Caenorhabditis elegans

<400> SEQUENCE: 4

```
Met Asn Asp Ser Ile Asp Asp Phe Pro Pro Glu Pro Arg Gly Arg
 1               5                  10                 15

Cys Tyr Thr Trp Pro Met Gln Gln Tyr Ile Tyr Gln Glu Ser Ser Ala
             20                  25                  30

Thr Ile Pro His His His Leu Asn Gln His Asn Asn Pro Tyr His Pro
         35                  40                  45

Met His Pro His His Gln Leu Pro His Met Gln Gln Leu Pro Gln Pro
     50                  55                  60

Leu Leu Asn Leu Asn Met Thr Thr Leu Thr Ser Ser Gly Ser Ser Val
 65                  70                  75                  80

Ala Ser Ser Ile Gly Gly Gly Ala Gln Cys Ser Pro Cys Ala Ser Gly
                 85                  90                  95

Ser Ser Thr Ala Ala Thr Asn Ser Ser Gln Gln Gln Thr Val Gly
            100                 105                 110

Gln Met Leu Ala Ala Ser Val Pro Cys Ser Ser Gly Met Thr Leu
        115                 120                 125

Gly Met Ser Leu Asn Leu Ser Gln Gly Gly Pro Met Pro Ala Lys
    130                 135                 140

Lys Lys Arg Cys Arg Lys Lys Pro Thr Asp Gln Leu Ala Gln Lys Lys
145                 150                 155                 160

Pro Asn Pro Trp Gly Glu Glu Ser Tyr Ser Asp Ile Ile Ala Lys Ala
                165                 170                 175

Leu Glu Ser Ala Pro Asp Gly Arg Leu Lys Leu Asn Glu Ile Tyr Gln
            180                 185                 190
```

```
Trp Phe Ser Asp Asn Ile Pro Tyr Phe Gly Glu Arg Ser Ser Pro Glu
        195                 200                 205

Glu Ala Ala Gly Trp Lys Asn Ser Ile Arg His Asn Leu Ser Leu His
    210                 215                 220

Ser Arg Phe Met Arg Ile Gln Asn Glu Gly Ala Gly Lys Ser Ser Trp
225                 230                 235                 240

Trp Val Ile Asn Pro Asp Ala Lys Pro Gly Arg Asn Pro Arg Arg Thr
                245                 250                 255

Arg Glu Arg Ser Asn Thr Ile Glu Thr Thr Lys Ala Gln Leu Glu
                260                 265                 270

Lys Ser Arg Arg Gly Ala Lys Lys Arg Ile Lys Glu Arg Ala Leu Met
            275                 280                 285

Gly Ser Leu His Ser Thr Leu Asn Gly Asn Ser Ile Ala Gly Ser Ile
        290                 295                 300

Gln Thr Ile Ser His Asp Leu Tyr Asp Asp Ser Met Gln Gly Ala
305                 310                 315                 320

Phe Asp Asn Val Pro Ser Ser Phe Arg Pro Arg Thr Gln Ser Asn Leu
                325                 330                 335

Ser Ile Pro Gly Ser Ser Arg Val Ser Pro Ala Ile Gly Ser Asp
            340                 345                 350

Ile Tyr Asp Asp Leu Glu Phe Pro Ser Trp Val Gly Glu Ser Val Pro
        355                 360                 365

Ala Ile Pro Ser Asp Ile Val Asp Arg Thr Asp Gln Met Arg Ile Asp
            370                 375                 380

Ala Thr Thr His Ile Gly Gly Val Gln Ile Lys Gln Glu Ser Lys Pro
385                 390                 395                 400

Ile Lys Thr Glu Pro Ile Ala Pro Pro Ser Tyr His Glu Leu Asn
                405                 410                 415

Ser Val Arg Gly Ser Cys Ala Gln Asn Pro Leu Leu Arg Asn Pro Ile
            420                 425                 430

Val Pro Ser Thr Asn Phe Lys Pro Met Pro Leu Pro Gly Ala Tyr Gly
        435                 440                 445

Asn Tyr Gln Asn Gly Gly Ile Thr Pro Ile Asn Trp Leu Ser Thr Ser
    450                 455                 460

Asn Ser Ser Pro Leu Pro Gly Ile Gln Ser Cys Gly Ile Val Ala Ala
465                 470                 475                 480

Gln His Thr Val Ala Ser Ser Ala Leu Pro Ile Asp Leu Glu Asn
                485                 490                 495

Leu Thr Leu Pro Asp Gln Pro Leu Met Asp Thr Met Asp Val Asp Ala
            500                 505                 510

Leu Ile Arg His Glu Leu Ser Gln Ala Gly Gly Gln His Ile His Phe
        515                 520                 525

Asp Leu
    530

<210> SEQ ID NO 5
<211> LENGTH: 3441
<212> TYPE: DNA
<213> ORGANISM: Caenorhabditis elegans

<400> SEQUENCE: 5
atgcatgtta acattttaca tccacaactg caaacgatgg tcgagcagtg gcaaatgcga      60
gaacgcccat cgctggagac cgagaatggc aaaggatcgc tgctcctgga aaatgaaggt     120
gtcgcagata tcatcactat gtgtccattc ggagaagtta ttagtgtagt atttccgtgg     180
```

-continued

| | |
|---|---|
| tttcttgcaa atgtgcgaac atcgctagaa atcaagctat cagatttcaa acatcaactt | 240 |
| ttcgaattga ttgctccgat gaagtgggga acatattccg taaagccaca ggattatgtg | 300 |
| ttcagacagt tgaataattt cggcgaaatt gaagttatat ttaacgacga tcaaccctg | 360 |
| tcgaaattag agctccacgg cactttccca atgcttttc tctaccaacc tgatggaata | 420 |
| aacagggata agaattaat gagtgatata agtcattgtc taggatactc actggataaa | 480 |
| ctggaagaga gcctcgatga ggaactccgt caatttcgtg cttctctctg ggctcgtacg | 540 |
| aagaaaacgt gcttgacacg tggacttgag ggtaccagtc actacgcgtt ccccgaagaa | 600 |
| cagtacttgt gtgttggtga atcgtgcccg aaagatttgg aatcaaaagt caaggctgcc | 660 |
| aagctgagtt atcagatgtt ttggagaaaa cgtaaagcgg aaatcaatgg agtttgcgag | 720 |
| aaaatgatga agattcaaat tgaattcaat ccgaacgaaa ctccgaaatc tctgcttcac | 780 |
| acgtttctct acgaaatgcg aaaattggat gtatacgata ccgatgatcc tgcagatgaa | 840 |
| ggatggtttc ttcaattggc tggacgtacc acgtttgtta caaatccaga tgtcaaactt | 900 |
| acgtcttatg atggtgtccg ttcggaactg gaaagctatc gatgccctgg attcgttgtt | 960 |
| cgccgacaat cactagtcct caaagactat tgtcgcccaa accactcta cgaaccacat | 1020 |
| tatgtgagag cacacgaacg aaaacttgct ctagacgtgc tcagcgtgtc tatagatagc | 1080 |
| acaccaaaac agagcaagaa cagtgacatg gttatgactg attttcgtcc gacagcttca | 1140 |
| ctcaaacaag tttcactttg ggaccttgac gcgaatctta tgatacgcc tgtgaatatt | 1200 |
| tctggattcg atttcccggc cgacgtggat atgtacgttc gaatcgaatt cagtgtatat | 1260 |
| gtggggacac tgacgctggc atcaaaatct acaacaaaag tgaatgctca atttgcaaaa | 1320 |
| tggaataagg aaatgtacac ttttgatcta tacatgaagg atatgccacc atctgcagta | 1380 |
| ctcagcattc gtgttttgta cggaaaagtg aaattaaaaa gtgaagaatt cgaagttggt | 1440 |
| tgggtaaata tgtccctaac cgattgggaga gatgaactac gacaaggaca atttttattc | 1500 |
| catctgtggg ctcctgaacc gactgccaat cgtagtagga tcggagaaaa tggagcaagg | 1560 |
| ataggcacca acgcagcggt tacaattgaa atctcaagtt atggtggtag agttcgaatg | 1620 |
| ccgagtcaag gacaatacac atatctcgtc aagcaccgaa gtacttggac ggaaactttg | 1680 |
| aatattatgg gtgatgacta tgagtcgtgt atcagagatc caggatataa gaagcttcag | 1740 |
| atgcttgtca agaagcatga atctggaatt gtattagagg aagatgaaca acgtcatgtc | 1800 |
| tggatgtgga ggagatacat tcaaaagcag gagcctgatt tgctcattgt gctctccgaa | 1860 |
| ctcgcatttg tgtggactga tcgtgagaac ttttccgagc tctatgtgat gcttgaaaaa | 1920 |
| tggaaaccgc cgagtgtggc agccgcgttg actttgcttg gaaaacgttg cacggatcgt | 1980 |
| gtgattcgaa agtttgcagt ggagaagttg aatgagcagc tgagcccggt cacattccat | 2040 |
| cttttcatat tgcctctcat acaggcgttg aagtacgaac cgcgtgctca atcggaagtt | 2100 |
| ggaatgatgc tcttgactag agctctctgc gattatcgaa ttggacatcg acttttctgg | 2160 |
| ctgctccgtg cagagattgc tcgtttgaga gattgtgatc tgaaaagtga agaatatcgc | 2220 |
| cgtatctcac ttctgatgga agcttacctc cgtggaaatg aagagcacat caagatcatc | 2280 |
| acccgacaag ttgacatggt tgatgagctc acacgaatca gcactcttgt caaaggaatg | 2340 |
| ccaaaagatg ttgctacgat gaaactgcgt gacgagcttc gatcgattag tcataaaatg | 2400 |
| gaaaatatgg attctccact ggatcctgtg tacaaactgg gtgaaatgat aatcgacaaa | 2460 |
| gccatcgtcc taggaagtgc aaaacgtccg ttaatgcttc actggaagaa caaaaatcca | 2520 |

```
aagagtgacc tgcaccttcc gttctgtgca atgatcttca agaatggaga cgatcttcgc    2580
caggacatgc ttgttcttca agttctcgaa gttatggata acatctggaa ggctgcaaac    2640
attgattgct gtttgaaccc gtacgcagtt cttccaatgg gagaaatgat tggaattatt    2700
gaagttgtgc ctaattgtaa aacaatattc gagattcaag ttggaacagg attcatgaat    2760
acagcagttc ggagtattga tccttcgttt atgaataagt ggattcggaa acaatgcgga    2820
attgaagatg aaagaagaa aagcaaaaag gactctacga aaaatcccat cgaaaagaag    2880
attgataata ctcaagccat gaagaaatat tttgaaagtg tcgatcgatt cctatactcg    2940
tgtgttggat attcagttgc cacgtacata atgggaatca aggatcgtca cagtgataat    3000
ctgatgctca ctgaagatgg aaaatatttc cacattgatt tcggtcacat tttgggacac    3060
ggaaagacca aacttgggat ccagcgagat cgtcaaccgt ttattctaac cgaacacttt    3120
atgacagtga ttcgatcggg taaatctgtg gatggaaatt cgcatgagct acaaaaattc    3180
aaaacgttat gcgtcgaagc ctacgaagta atgtggaata atcgagattt gttcgtttcc    3240
ttgttcacct tgatgctcgg aatggagttg cctgagctgt cgacgaaagc ggatttggat    3300
catttgaaga aaccctctt ctgcaatgga gaaagcaaag aagaagcgag aaagttttc    3360 gctggaatct acgaagaagc cttcaatgga tcatggtcta ccaaaacgaa ttggctcttc    3420
cacgcagtca aacactactg a                                              3441
```

<210> SEQ ID NO 6
<211> LENGTH: 1146
<212> TYPE: PRT
<213> ORGANISM: Caenorhabditis elegans

<400> SEQUENCE: 6

```
Met His Val Asn Ile Leu His Pro Gln Leu Gln Thr Met Val Glu Gln
1               5                   10                  15

Trp Gln Met Arg Glu Arg Pro Ser Leu Glu Thr Glu Asn Gly Lys Gly
            20                  25                  30

Ser Leu Leu Leu Glu Asn Glu Gly Val Ala Asp Ile Ile Thr Met Cys
        35                  40                  45

Pro Phe Gly Glu Val Ile Ser Val Val Phe Pro Trp Phe Leu Ala Asn
    50                  55                  60

Val Arg Thr Ser Leu Glu Ile Lys Leu Ser Asp Phe Lys His Gln Leu
65                  70                  75                  80

Phe Glu Leu Ile Ala Pro Met Lys Trp Gly Thr Tyr Ser Val Lys Pro
                85                  90                  95

Gln Asp Tyr Val Phe Arg Gln Leu Asn Asn Phe Gly Glu Ile Glu Val
            100                 105                 110

Ile Phe Asn Asp Asp Gln Pro Leu Ser Lys Leu Glu Leu His Gly Thr
        115                 120                 125

Phe Pro Met Leu Phe Leu Tyr Gln Pro Asp Gly Ile Asn Arg Asp Lys
    130                 135                 140

Glu Leu Met Ser Asp Ile Ser His Cys Leu Gly Tyr Ser Leu Asp Lys
145                 150                 155                 160

Leu Glu Glu Ser Leu Asp Glu Leu Arg Gln Phe Arg Ala Ser Leu
                165                 170                 175

Trp Ala Arg Thr Lys Lys Thr Cys Leu Thr Arg Gly Leu Glu Gly Thr
            180                 185                 190

Ser His Tyr Ala Phe Pro Glu Glu Gln Tyr Leu Cys Val Gly Glu Ser
        195                 200                 205
```

-continued

```
Cys Pro Lys Asp Leu Glu Ser Lys Val Lys Ala Ala Lys Leu Ser Tyr
    210                 215                 220
Gln Met Phe Trp Arg Lys Arg Lys Ala Glu Ile Asn Gly Val Cys Glu
225                 230                 235                 240
Lys Met Met Lys Ile Gln Ile Glu Phe Asn Pro Asn Glu Thr Pro Lys
                245                 250                 255
Ser Leu Leu His Thr Phe Leu Tyr Glu Met Arg Lys Leu Asp Val Tyr
            260                 265                 270
Asp Thr Asp Asp Pro Ala Asp Glu Gly Trp Phe Leu Gln Leu Ala Gly
        275                 280                 285
Arg Thr Thr Phe Val Thr Asn Pro Asp Val Lys Leu Thr Ser Tyr Asp
    290                 295                 300
Gly Val Arg Ser Glu Leu Glu Ser Tyr Arg Cys Pro Gly Phe Val Val
305                 310                 315                 320
Arg Arg Gln Ser Leu Val Leu Lys Asp Tyr Cys Arg Pro Lys Pro Leu
                325                 330                 335
Tyr Glu Pro His Tyr Val Arg Ala His Glu Arg Lys Leu Ala Leu Asp
            340                 345                 350
Val Leu Ser Val Ser Ile Asp Ser Thr Pro Lys Gln Ser Lys Asn Ser
        355                 360                 365
Asp Met Val Met Thr Asp Phe Arg Pro Thr Ala Ser Leu Lys Gln Val
    370                 375                 380
Ser Leu Trp Asp Leu Asp Ala Asn Leu Met Ile Arg Pro Val Asn Ile
385                 390                 395                 400
Ser Gly Phe Asp Phe Pro Ala Asp Val Asp Met Tyr Val Arg Ile Glu
                405                 410                 415
Phe Ser Val Tyr Val Gly Thr Leu Thr Leu Ala Ser Lys Ser Thr Thr
            420                 425                 430
Lys Val Asn Ala Gln Phe Ala Lys Trp Asn Lys Glu Met Tyr Thr Phe
        435                 440                 445
Asp Leu Tyr Met Lys Asp Met Pro Pro Ser Ala Val Leu Ser Ile Arg
    450                 455                 460
Val Leu Tyr Gly Lys Val Lys Leu Lys Ser Glu Glu Phe Glu Val Gly
465                 470                 475                 480
Trp Val Asn Met Ser Leu Thr Asp Trp Arg Asp Glu Leu Arg Gln Gly
                485                 490                 495
Gln Phe Leu Phe His Leu Trp Ala Pro Glu Pro Thr Ala Asn Arg Ser
            500                 505                 510
Arg Ile Gly Glu Asn Gly Ala Arg Ile Gly Thr Asn Ala Ala Val Thr
        515                 520                 525
Ile Glu Ile Ser Ser Tyr Gly Gly Arg Val Arg Met Pro Ser Gln Gly
    530                 535                 540
Gln Tyr Thr Tyr Leu Val Lys His Arg Ser Thr Trp Thr Glu Thr Leu
545                 550                 555                 560
Asn Ile Met Gly Asp Asp Tyr Glu Ser Cys Ile Arg Asp Pro Gly Tyr
                565                 570                 575
Lys Lys Leu Gln Met Leu Val Lys Lys His Glu Ser Gly Ile Val Leu
            580                 585                 590
Glu Glu Asp Glu Gln Arg His Val Trp Met Trp Arg Arg Tyr Ile Gln
        595                 600                 605
Lys Gln Glu Pro Asp Leu Leu Ile Val Leu Ser Glu Leu Ala Phe Val
    610                 615                 620
Trp Thr Asp Arg Glu Asn Phe Ser Glu Leu Tyr Val Met Leu Glu Lys
```

-continued

```
            625             630             635             640
Trp Lys Pro Pro Ser Val Ala Ala Leu Thr Leu Leu Gly Lys Arg
                645             650             655
Cys Thr Asp Arg Val Ile Arg Lys Phe Ala Val Glu Lys Leu Asn Glu
                660             665             670
Gln Leu Ser Pro Val Thr Phe His Leu Phe Ile Leu Pro Leu Ile Gln
                675             680             685
Ala Leu Lys Tyr Glu Pro Arg Ala Gln Ser Glu Val Gly Met Met Leu
    690             695             700
Leu Thr Arg Ala Leu Cys Asp Tyr Arg Ile Gly His Arg Leu Phe Trp
705             710             715             720
Leu Leu Arg Ala Glu Ile Ala Arg Leu Arg Asp Cys Asp Leu Lys Ser
                725             730             735
Glu Glu Tyr Arg Arg Ile Ser Leu Leu Met Glu Ala Tyr Leu Arg Gly
                740             745             750
Asn Glu Glu His Ile Lys Ile Ile Thr Arg Gln Val Asp Met Val Asp
                755             760             765
Glu Leu Thr Arg Ile Ser Thr Leu Val Lys Gly Met Pro Lys Asp Val
    770             775             780
Ala Thr Met Lys Leu Arg Asp Glu Leu Arg Ser Ile Ser His Lys Met
785             790             795             800
Glu Asn Met Asp Ser Pro Leu Asp Pro Val Tyr Lys Leu Gly Glu Met
                805             810             815
Ile Ile Asp Lys Ala Ile Val Leu Gly Ser Ala Lys Arg Pro Leu Met
                820             825             830
Leu His Trp Lys Asn Lys Asn Pro Lys Ser Asp Leu His Leu Pro Phe
                835             840             845
Cys Ala Met Ile Phe Lys Asn Gly Asp Asp Leu Arg Gln Asp Met Leu
    850             855             860
Val Leu Gln Val Leu Glu Val Met Asp Asn Ile Trp Lys Ala Ala Asn
865             870             875             880
Ile Asp Cys Cys Leu Asn Pro Tyr Ala Val Leu Pro Met Gly Glu Met
                885             890             895
Ile Gly Ile Ile Glu Val Val Pro Asn Cys Lys Thr Ile Phe Glu Ile
                900             905             910
Gln Val Gly Thr Gly Phe Met Asn Thr Ala Val Arg Ser Ile Asp Pro
    915             920             925
Ser Phe Met Asn Lys Trp Ile Arg Lys Gln Cys Gly Ile Glu Asp Glu
    930             935             940
Lys Lys Lys Ser Lys Lys Asp Ser Thr Lys Asn Pro Ile Glu Lys Lys
945             950             955             960
Ile Asp Asn Thr Gln Ala Met Lys Lys Tyr Phe Glu Ser Val Asp Arg
                965             970             975
Phe Leu Tyr Ser Cys Val Gly Tyr Ser Val Ala Thr Tyr Ile Met Gly
                980             985             990
Ile Lys Asp Arg His Ser Asp Asn  Leu Met Leu Thr Glu  Asp Gly Lys
                995             1000            1005
Tyr Phe  His Ile Asp Phe Gly  His Ile Leu Gly His  Gly Lys Thr
    1010            1015            1020
Lys Leu  Gly Ile Gln Arg Asp  Arg Gln Pro Phe Ile  Leu Thr Glu
    1025            1030            1035
His Phe  Met Thr Val Ile Arg  Ser Gly Lys Ser Val  Asp Gly Asn
    1040            1045            1050
```

```
Ser His Glu Leu Gln Lys Phe Lys Thr Leu Cys Val Glu Ala Tyr
    1055            1060                1065

Glu Val Met Trp Asn Asn Arg Asp Leu Phe Val Ser Leu Phe Thr
    1070            1075                1080

Leu Met Leu Gly Met Glu Leu Pro Glu Leu Ser Thr Lys Ala Asp
    1085            1090                1095

Leu Asp His Leu Lys Lys Thr Leu Phe Cys Asn Gly Glu Ser Lys
    1100            1105                1110

Glu Glu Ala Arg Lys Phe Phe Ala Gly Ile Tyr Glu Glu Ala Phe
    1115            1120                1125

Asn Gly Ser Trp Ser Thr Lys Thr Asn Trp Leu Phe His Ala Val
    1130            1135                1140

Lys His Tyr
    1145
```